United States Patent [19]

Tanihara et al.

[11] Patent Number: 5,171,837
[45] Date of Patent: Dec. 15, 1992

[54] PEPTIDE CAPABLE OF BINDING INTERLEUKIN 6 AND AN ADSORBENT COMPRISING THE PEPTIDE IMMOBILIZED ON A CARRIER

[75] Inventors: Masao Tanihara; Kiichiro Oka, both of Kurashiki, Japan

[73] Assignee: Kuraray Co., Ltd., Okayama, Japan

[21] Appl. No.: 582,831

[22] PCT Filed: Feb. 6, 1990

[86] PCT No.: PCT/JP90/00142
§ 371 Date: Oct. 5, 1990
§ 102(e) Date: Oct. 5, 1990

[87] PCT Pub. No.: WO90/09396
PCT Pub. Date: Aug. 23, 1990

[30] Foreign Application Priority Data

Feb. 8, 1989 [JP] Japan .................................. 1-30738
Oct. 18, 1989 [JP] Japan .................................. 1-272254

[51] Int. Cl.$^5$ .......................... C07K 7/08; C07K 7/10; C07K 17/00
[52] U.S. Cl. .................................. 530/324; 530/325; 530/326; 530/810
[58] Field of Search ................. 424/85.2, 484; 514/12, 514/13; 530/324, 325, 326, 810, 811, 814, 815, 816, 415; 604/5, 6

[56] References Cited

U.S. PATENT DOCUMENTS

| | | | |
|---|---|---|---|
| 4,581,010 | 4/1986 | Skurkovich et al. | 604/5 |
| 4,605,394 | 8/1986 | Skurkovich | 604/5 |
| 4,737,544 | 4/1988 | McCain et al. | 604/6 |

FOREIGN PATENT DOCUMENTS 0255206 5/1987 European Pat. Off. .
63-154700 6/1988 Japan .
0045064 2/1990 Japan .

OTHER PUBLICATIONS

Medical Immunology, vol. 15 (2), 1988, (partial translation), pp. 195-201.
Nature, vol. 299, 1982, pp. 793-797, London, GB; M. Noda et al.: "Primary Structure of α-Subunit Precursor of Torpedo Califonica Acetylcholine Receptor Deduced from cDNA Sequence".
Int. Arch. Allergy Appl. Imunol., vol. 88, 1989, pp. 29-33, Basel, CH, & 17th Int. Symp. of the Collegium Internationale Allergologium, Port-de-France, Mar. 5-10, 1988; T. Hirano et al.: "A Multifunctional Cytokine (IL-6/BSF-2) and Its Receptor".
Science, (Washington, D.C., 1983—), vol. 241, No. 4867, (1988), Katsuhiko Yamasaki et al., [Cloning and Expression of the Human Interleukin-6 (BSF-2/IFNβ 2) Receptor], pp. 825-828.
Proc. Jpn. Acad. Ser. B Phys. Biol. Sci., vol. 64, No. 7, (1988), Katsuhiko Yamasaki et al., [Molecular Structure of Interleukin 6 Receptor], pp. 209-211.
T. Creighton, *Proteins*, pp. 53-54, 1983.
G. Tosato et al., pp. 157-161 in *Therapeutic Peptides and Proteins*, Marshak and Liu, editors, 1989.

*Primary Examiner*—Robert A. Wax
*Assistant Examiner*—Stephen Walsh
*Attorney, Agent, or Firm*—Wegner, Cantor, Mueller & Player

[57] ABSTRACT

A peptide being capable of binding to interleukin 6, and an adsorbent for interleukin 6 comprising the peptide immobilized on a carrier.

26 Claims, No Drawings

PEPTIDE CAPABLE OF BINDING INTERLEUKIN 6 AND AN ADSORBENT COMPRISING THE PEPTIDE IMMOBILIZED ON A CARRIER

FIELD OF THE INVENTION

The present invention relates to a peptide being capable of binding to interleukin 6, and an adsorbent for interleukin 6 comprising the peptide immobilized on a carrier.

It is known that interleukin 6 (hereinafter abbreviated as IL-6) acts on lymphocytes which are capable of producing an antibody to remarkably enhance productivity of the antibody, and IL-6 is considered to be one of causative agents of autoimmune diseases such as rheumatism and the like. Accordingly, the peptide and the adsorbent of the present invention are useful for treatment of autoimmune diseases such as rheumatism and the like.

PRIOR ART

Science, Vol. 241, pages 825 to 828 (1988) reports that a precursor of human interleukin 6 receptor (hereinafter abbreviated as IL-6 receptor) is composed of 468 amino acids and its primary structure has been elucidated. According to this report, the primary structure of a mature type IL-6 receptor is represented by the formula:

| | | | | | | | | | | | | |
|---|---|---|---|---|---|---|---|---|---|---|---|---|
| Leu | Ala | Pro | Arg | Arg | Cys | Pro | Ala | Gln | Glu | Val | Ala | Arg |
| Gly | Val | Leu | Thr | Ser | Leu | Pro | Gly | Asp | Ser | Val | Thr | Leu |
| Thr | Cys | Pro | Gly | Val | Glu | Pro | Glu | Asp | Asn | Ala | Thr | Val |
| His | Trp | Val | Leu | Arg | Lys | Pro | Ala | Ala | Gly | Ser | His | Pro |
| Ser | Arg | Trp | Ala | Gly | Met | Gly | Arg | Arg | Leu | Leu | Leu | Arg |
| Ser | Val | Gln | Leu | His | Asp | Ser | Gly | Asn | Tyr | Ser | Cys | Tyr |
| Arg | Ala | Gly | Arg | Pro | Ala | Gly | Thr | Val | His | Leu | Leu | Val |
| Asp | Val | Pro | Pro | Glu | Glu | Pro | Gln | Leu | Ser | Cys | Phe | Arg |
| Lys | Ser | Pro | Leu | Ser | Asn | Val | Val | Cys | Glu | Trp | Gly | Pro |
| Arg | Ser | Thr | Pro | Ser | Leu | Thr | Thr | Lys | Ala | Val | Leu | Leu |
| Val | Arg | Lys | Phe | Gln | Asn | Ser | Pro | Ala | Glu | Asp | Phe | Gln |
| Glu | Pro | Cys | Gln | Tyr | Ser | Gln | Glu | Ser | Gln | Lys | Phe | Ser |
| Cys | Gln | Leu | Ala | Val | Pro | Glu | Gly | Asp | Ser | Ser | Phe | Tyr |
| ILe | Val | Ser | Met | Cys | Val | Ala | Ser | Ser | Val | Gly | Ser | Lys |
| Phe | Ser | Lys | Thr | Gln | Thr | Phe | Gln | Gly | Cys | Gly | Ile | Leu |
| Gln | Pro | Asp | Pro | Pro | Ala | Asn | Ile | Thr | Val | Thr | Ala | Val |
| Ala | Arg | Asn | Pro | Arg | Trp | Leu | Ser | Val | Thr | Trp | Gln | Asp |
| Pro | His | Ser | Trp | Asn | Ser | Ser | Phe | Tyr | Arg | Leu | Arg | Phe |
| Glu | Leu | Arg | Tyr | Arg | Ala | Glu | Arg | Ser | Lys | Thr | Phe | Thr |
| Thr | Trp | Met | Val | Lys | Asp | Leu | Gln | His | His | Cys | Val | Ile |
| His | Asp | Ala | Trp | Ser | Gly | Leu | Arg | His | Val | Val | Gln | Leu |
| Arg | Ala | Gln | Glu | Glu | Phe | Gly | Gln | Gly | Glu | Trp | Ser | Glu |
| Trp | Ser | Pro | Glu | Ala | Met | Gly | Thr | Pro | Trp | Thr | Glu | Ser |
| Arg | Ser | Pro | Pro | Ala | Glu | Asn | Glu | Val | Ser | Thr | Pro | Met |
| Gln | Ala | Leu | Thr | Thr | Asn | Lys | Asp | Asp | Asp | Asn | Ile | Leu |
| Phe | Arg | Asp | Ser | Ala | Asn | Ala | Thr | Ser | Leu | Pro | Val | Gln |
| Asp | Ser | Ser | Ser | Val | Pro | Leu | Pro | Thr | Phe | Leu | Val | Ala |
| Gly | Gly | Ser | Leu | Ala | Phe | Gly | Thr | Leu | Leu | Cys | Ile | Ala |
| Ile | Val | Leu | Arg | Phe | Lys | Lys | Thr | Trp | Lys | Leu | Arg | Ala |
| Leu | Lys | Glu | Gly | Lys | Thr | Ser | Met | His | Pro | Pro | Tyr | Ser |
| Leu | Gly | Gln | Leu | Val | Pro | Glu | Arg | Pro | Arg | Pro | Thr | Pro |
| Val | Leu | Val | Pro | Leu | Ile | Ser | Pro | Pro | Val | Ser | Pro | Ser |
| Ser | Leu | Gly | Ser | Asp | Asn | Thr | Ser | Ser | His | Asn | Arg | Pro |
| Asp | Ala | Arg | Asp | Pro | Arg | Ser | Pro | Tyr | Asp | Ile | Ser | Asn |
| Thr | Asp | Tyr | Phe | Phe | Pro | Arg | | | | | | |

Further, Medical Immunology, Vol. 15, pates 195 to 201 (1988) discloses a report of a relation between IL-6 and autoimmune diseases.

In treatment of autoimmune diseases such as rheumatism and the like, it has been requested to establish means for removing IL-6 which is considered to be a main caustive agent of such diseases. However, any practical method thereof has not yet been established.

One object of the present invention is to provide a novel peptide being capable of binding IL-6. Another object of the present invention is to provide an adsorbent for IL-6 comprising the novel peptide immobilized on a carrier.

DISCLOSURE OF THE INVENTION

According to the present invention, there is provided (1) a peptide being capable of binding to IL-6 represented by the general formula:

$$\text{H-X-A-Y-Z} \quad [I]$$

[wherein A is a peptide segment formed by bonding 6 to 50 amino acids; each of X and Y is a single bond or an amino acid residue selected from the group consisting of Asp, Glu, Lys, Ala and a divalent group of the formula: $-\text{NH}(\text{CH}_2)_n-\text{CO}-$ (wherein n is an integer of 1 to 17), or a peptide-segment composed of 2 to 10 amino acid residues selected from the above group which are bound to each other through a peptide bond; Z is hydroxyl group or amino group]. Further, according to the present invention, there is provided (2) an adsorbent comprising the peptide immobilized on a carrier.

In the present specification, various amino acid residues are abbreviated as follows:

Ala: L-alanine residue,
Arg: L-arginine residue,
Asn: L-asparagine residue,
Asp: L-aspartic acid residue,
Cys: L-cysteine residue,
Gln: L-glutamine residue,
Glu: L-glutamic acid residue,
Gly: glycine residue,
His: L-histidine residue,
Ile: L-isoleucine residue,
Leu: L-leucine residue,
Lys: L-lysine residue,
Phe: L-phenylalanine residue, Pro: L-proline residue,
Ser: L-serine residue,
Thr: L-threonine residue,
Trp: L-tryptophan residue,
Tyr: L-tyrosine residue,
Val: L-valine residue.

Further, in the present specification, the amino acid sequence is described in such a manner that the amino acid residue at the N-terminal is located on the left hand and the amino acid residue at the C-terminal is located on the right hand according to the conventional method.

As the peptide segment represented by X and Y in the general formula (I), for Example, there are the following peptide segments:

—Ala—Gly—, —Asp—Asp—, —Glu—Glu—, —Lys—Lys—, —Asp—Ala—, —Gly—Gly—, $+\text{NH(CH}_2)_{11}\text{C}+_2$, $+\text{NH(CH}_2)_{17}\text{C}+_2$, —Ala—Lys—, —Asp—Glu—, —Asp—Gly—, —Glu—Asp—,
       $\|$                $\|$
       O                   O —Glu—Lys—, —Lys—Gly—, —Lys—NH(CH$_2$)$_{11}$C—, —Gly—Asp—, —Gly—Lys—, —NH(CH$_2$)$_{11}$C—Glu—,
                                    $\|$                                              $\|$
                                    O                                                 O —NH(CH$_2$)$_{11}$C—Lys—, —NH(CH$_2$)$_{17}$C—Asp—, —NH(CH$_2$)$_{17}$C—Lys—, —Lys—Lys—Gly—,
         $\|$                      $\|$                       $\|$
         O                         O                          O —Ala—Ala—Lys—, $+\text{Asp}+_5$, $+\text{Glu}+_5$, $+\text{Lys}+_5$, $+\text{Gly}+_5$, $+\text{Ala}+_5$, $+\text{NH(CH}_2)_{11}\text{C}+_5$, $+\text{NH(CH}_2)_{17}\text{C}+_5$, —Lys—Asp—Glu—Gly—NH(CH$_2$)$_{17}$C—, —Gly—Lys—Glu—Glu—Asp—,
       $\|$                $\|$                                                 $\|$
       O                   O                                                    O —Asp—Glu—NH(CH$_2$)$_{17}$C—Lys—Gly—Lys—, $+\text{Asp}+_{10}$, $+\text{Ala}+_{10}$, $+\text{Glu}+_{10}$, $+\text{Lys}+_{10}$,
              $\|$
              O $+\text{Gly}+_{10}$, $+\text{NH(CH}_2)_{11}\text{C}+_{10}$, $+\text{NH(CH}_2)_{17}\text{C}+_{10}$, —Lys—Glu—Gly—NH(CH$_2$)$_{11}$C—Asp—Asp—Lys—Lys—Glu—Gly,
                       $\|$
                       O —Lys—Glu—Glu—Gly—Asp—Asp—Lys—Lys—Gly—Gly When the peptide represented by the general formula (I) wherein X and/or Y are peptide segments composed of 11 or more amino acid residues selected from the above group which are bound to each other through a peptide bond, such a peptide may not have ability to bind the desired IL-6.

Suitable examples of the peptide segment represented by A in the general formula (I) are as follows. The amino acid residues of each peptide segment may be those subjected to homologous substitution.

—Thr—Ser—Leu—Pro—Gly—Asp—Ser—Val—Thr  (a)
—Leu—Thr—Cys—Pro—Gly—Val—Glu—Pro—Glu
—Asp—

—Gly—Thr—Val—His—Leu—Leu—Val—Asp—Val  (b)
—Pro—Pro—Glu—Glu—Pro—Gln—Leu—Ser—Cys
—Phe—Arg—Lys—

—Ser—Thr—Pro—Ser—Leu—Thr—Thr—Lys—Ala  (c)
—Val—Leu—Leu—Val—Arg—Lys—Phe—Gln—Asn
—Ser—Pro—Ala—Glu—Asp—

—Arg—Lys—Phe—Gln—Asn—Ser—Pro—Ala—Glu  (d)
—Asp—Phe—Gln—Glu—Pro—Cys—Gln—Tyr—Ser
—Gln—Glu—Ser—

—Asn—Pro—Arg—Trp—Leu—Ser—Val—Thr—Trp  (e)
—Gln—Asp—Pro—His—Ser—

—Trp—Asn—Ser—Ser—Phe—Tyr—Arg—Leu—Arg  (f)
—Phe—Glu—Leu—Arg—Tyr—Arg—Ala—Glu—Arg
—Ser—Lys—

—Gln—Ala—Leu—Thr—Thr—Asn—Lys—Asp—Asp  (g)
—Asp—Asn—Ile—Leu—Phe—Arg—Asp—Ser—Ala—

—His—Ser—Trp—Asn—Ser—Ser—Phe—Tyr—Arg  (h)
—Leu—Arg—Phe—Glu—Leu—Arg—Tyr—Arg—Ala
—Glu—Arg—Ser—Lys—

—Pro—His—Ser—Trp—Asn—Ser—Ser—Phe—Tyr  (i)
—Arg—Leu—Arg—Phe—Glu—Leu—Arg—Tyr—Arg
—Ala—Glu—Arg—Ser—Lys—

—Asp—Pro—His—Ser—Trp—Asn—Ser—Ser—Phe  (j)
—Tyr—Arg—Leu—Arg—Phe—Glu—Leu—Arg—Tyr
—Arg—Ala—Glu—Arg—Ser—Lys—

—Gln—Asp—Pro—His—Ser—Trp—Asn—Ser—Ser—  (k)
—Phe—Tyr—Arg—Leu—Arg—Phe—Glu—Leu—Arg
—Tyr—Arg—Ala—Glu—Arg—Ser—Lys—

—Trp—Gln—Asp—Pro—His—Ser—Trp—Asn—Ser  (l)
—Ser—Phe—Tyr—Arg—Leu—Arg—Phe—Glu—Leu
—Arg—Tyr—Arg—Ala—Glu—Arg—Ser—Lys—

The peptide represented by the general formula (I) wherein A is a peptide segment formed by bonding 5 or less amino acids has no ability to bind IL-6, or its ability to bind IL-6 is insufficient for the practical use. Further, it is not practical to synthesize a peptide segment being capable of bonding to the desired IL-6 and formed by binding 51 or more amino acids.

The synthesis of the peptide of the general formula (I) can be carried out by the conventional method usually employed in peptide syntheses, for Example, a solid phase synthesis, or a liquid phase synthesis such as stepwise elongation, fragment condensation or the like. In view of the operation, a solid phase synthesis is convenient [see, for Example, Journal of the American Chemical Society, Vol. 85, pages 2149 to 2154 (1963); "Seikagaku Jikken Koza (Biochemical Experiment Lecture 1, Protein Chemistry IV, Chemical Modification and Peptide Synthesis)" edited by The Japanese Biochemical Society, published November 15, 1977 by Tokyo Kagaku Dojin Co., Ltd., pages 207 to 495; "ZokuSeikagaku Jikken Koza (Biochemical Experiment Lecture Second Series 2, Protein Chemistry, the last volume )" edited by The Japanese Biochemical Society, published May 20, 1987 by Tokyo Kagaku Dojin Co., Ltd, pages 641 to 694; etc.].

The production of the peptide of the general formula (I) according to a solid phase synthesis is carried out by using a polymer such as styrene-divinylbenzene copolymer which is insoluble in a reaction solvent as a solid phase carrier. An amino acid or amino acid amide corresponding to the C-terminal of the desired peptide is bound to the solid phase carrier by utilizing $\alpha$-COOH group or $\alpha$-CONH$_2$ group thereof. Then, corresponding amino acids or peptide segments are bound to the amino acid or amino acid amide in order through peptide bonds toward the direction of the N-terminal of the desired peptide. In this case, usually, the amino acid or peptide segment to be bound is added after protection of any functional group of the C-terminal other than $\alpha$-COOH group. In addition, usually, an amino acid, or amino acid amide or peptide segment on the solid phase carrier is subjected to a peptide bond formation reaction after removal of a protecting group only for the $\alpha$-NH$_2$ group. Formation of peptide bonds are carried out by a known method such as a dehydration condensation method using carbodiimide or the like. The desired peptide can be obtained by forming a peptide chain corresponding to the desired peptide on a solid phase carrier, removing it from the solid phase carrier and removing any protecting group from any protected functional group and, if necessary, purifying the resulting peptide. In this case, removal of the peptide chain from the solid phase carrier and removal of the protecting group can be carried out by a known method and it is preferred that these operations are carried out at once by using hydrogen fluoride from the viewpoint of inhibition of a side reaction. Further, the purification of the resulting peptide can be efficiently carried out by reversed phase liquid chromatography.

Since the peptide of the general formula (I) is capable of binding to IL-6, it can inhibit binding of IL-6 to its receptor. Therefore, the production of an autoantibody can be inhibited by administering the peptide of the general formula (I) to a patient suffering from autoimmune diseases such as rheumatism and the like, wherein the production of an autoantibody caused by binding IL-6 to its receptor is accelerated.

A dosage to manifest an effective activity of the peptide of the general formula (I) is not more than 2 g/kg, preferably, not less than 1 $\mu$g/kg to not more than 200 mg/kg. As preferred dosage forms and routes of administration, for Example, there is a solution of the peptide of the general formula (I) dissolved in water or a physiologically acceptable salt solution such as physiological saline solution [e.g., a solution obtained by dissolving 1 mg of the peptide of the general formula (I) in 100 ml of 5% glucose solution or the like] by intravenous administration, subcutaneous administration, intraperitoneal administration and the like.

Further, the peptide of the general formula (I), or the above solution in water or a salt solution can be administered orally in the form of a capsule or liposome. It can also be administered percutaneously in the form of an oil. The peptide of the general formula (I) dose not manifest a remarkable acute toxicity at the above dosage.

Furthermore, the peptide of the general formula (I) is immobilized on a carrier and is used as an adsorbent of IL-6. One or more peptides of the general formula (I) can be used for the immobilization.

As the carrier to be used for immobilizing the peptide of the general formula (I), that having a hydrophilic surface and a reactive functional group such as amino group, carboxyl group, hydroxyl group or the like which can be utilized to form a covalent bonding with the peptide is preferable. Further, when the peptide is used as an adsorbent to adsorb IL-6 in a body fluid of a patient with an autoimmune disease, the above carrier is preferably insoluble to the body fluid and porous. As the porous carrier having a wide effective area to adsorb IL-6, a carrier having an exclusion limit protein molecular weight of about $10^6$ to $10^9$ or an average pore diameter of about 50 to 1000 nanometer can be preferably used. The carrier can be in any desired form such as particles, fibers, sheets, hollow fibers and the like. As these carrier, there are organic carriers, for Example, cellulose carriers such as CM-Cellulofine CH (exclusion limit protein molecular weight: about $3 \times 10^6$, sold by Seikagaku Kogyo Co., Ltd.) and the like, polyvinyl alcohol carriers such as TSK-gel CM-Toyopearl 650C (exclusion limit protein molecular weight: $5 \times 10^6$, manufactured by Toso Co., Ltd.), polyacrylamide carriers such as CM-Trisacryl M (exclusion limit protein molecular weight: $1 \times 10^7$, manufactured by Pharmacia-LKB, Sweden) and the like, agarose carriers such as Sepharose CL4B (exclusion limit protein molecular weight: $2 \times 10^7$, manufactured by Pharmacia-LKB, Sweden) and the like; and inorganic carriers, for Example, porous glass such as CPG10-1000 (exclusion limit protein molecular weight: $1 \times 10^8$, manufactured by Electro-nucleonics Co., U.S.A.) and the like.

Immobilization of the peptide of the general formula (I) on the carrier can be carried out according to a method generally employed in immobilization of a peptide or protein on a carrier. As methods for immobilization, for example, there are: a method comprising reacting a carboxyl group contained in a carrier with N-hydroxysuccinimide to convert the carboxyl group into a succinimidoxycarbonyl group and reacting this with the peptide of the general formula (I) at the amino group site (activated ester method); a method comprising condensing an amino group or a carboxyl group contained in a carrier with the peptide of the general formula (I) at the carboxyl group or amino group site in the presence of a condensation agent such as dicyclohexyl carbodiimide (condensation method); a method comprising crosslinking a carrier and the peptide of the general formula (I) with a compound having two or more functional groups such as glutaraldehyde (carrier crosslinking method), and the like. The adsorbent obtained by immobilizing the peptide of the general formula (I) on the carrier according to the activated ester method has the highest adsorption capability of IL-6. Usually, the amount of the peptide of the general formula (I) immobilized on the carrier should be about $3 \times 10^{-8}$ mole/g (carrier) or more so that the resulting adsorbent can adsorb a significant amount of IL-6, and about $1 \times 10^{-7}$ to $2 \times 10^{-6}$ mole/g (carrier) is preferable so that the peptide of the general formula (I) immobilized on the carrier can be efficiently utilized for adsorption of IL-6.

Removal of IL-6 can be carried out by contacting the adsorbent obtained by immobilizing the peptide of the general formula (I) on the carrier with a body fluid containing IL-6 such as blood, plasma, serum and the like to adsorb IL-6. For Example, the absorbent is used by packing it in a column. It is preferable that the column used for this purpose has inlet and outlet parts having the shape which can be easily connected to the blood circulation and is provided with filters of a material such as olyester between the inlet part and the adsorbent layer as well as between the outlet part and the adsorbent layer, respectively. Examples of the material for making the column include polyethylene, polypropylene, polycarbonate, polyester, polymethyl methacrylate and the like. Among these, polypropylene and polycarbonate are particularly suitable because the column packed with the adsorbent can be subjected to sterilization such as autoclave sterilization, γ ray-sterilization and the like before use.

For Example, removal of IL-6 from the body fluid of a patient using a column packed with the above adsorbent can be carried out according to an extracorporeal blood circulation system. As the extracorporeal blood circulation system, for Example, there are following two systems:

(1) Blood from the blood vessel of a patient is transferred to a column packed with the adsorbent, followed by removal of IL-6 from blood by adsorption in the column. The blood thus treated by passing through the column is then circulated in the blood vessel of the patient;

(2) Blood from the blood vessel of a patient is firstly separated into the blood cell component and the plasma component and the separated plasma component is transferred to a column packed with the adsorbent. IL-6 is removed from the plasma component by adsorption in the column. Then, the plasma component thus treated by passing through the column is admixed with the above separated blood cell component, and the resulting mixture is circulated in the blood vessel of the patient.

EMBODIMENT FOR WORKING THE INVENTION

The following Examples further illustrate the present invention in detail but are not to be construed to limit the scope thereof.

EXAMPLE 1

A peptide of the formula: H-Thr-Ser-Leu-Pro-Gly-Ser-Val-Thr-Leu-Thr-Cys-Pro-Gly-Val-Glu-Pro-Glu-Asp-Lys-OH was synthesized by using an automatic peptide synthesizer [manufactured by Applied Biosystems Corp., U.S.A., Model 430A] according to solid phase synthetic method.

That is, 0.13 g of a granular resin of a styrenedivinylbenzene copolymer [molar ratio of styrene to divinylbenzene being 99:1] containing 4-[N$^\alpha$-(t-butoxycarbonyl)-N$^\epsilon$-chlorbenzyloxycarbonyl)-L -lysyloxylmethyl]phenyacetamidomethyl group,

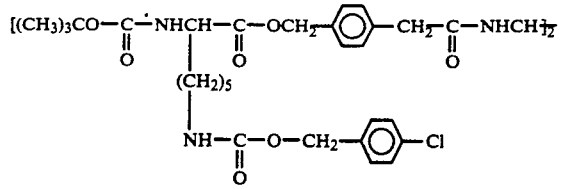

in a ratio of 0.78 mmole/g (resin) [manufactured by Applied Biosystems Corp., U.S.A., PAM Lysine, t-Boc-L-Lys (Cl-Z)] was used for binding the corresponding L-aspartic acid, L-cysteine, glycine, L-glutamic acid, L-leucine, L-serine, L-proline, L-threonine and L-valine thereto in order toward the direction of the N-terminal of the desired peptide according to a series of operation as shown in Table 1. In the condensation reaction, the above amino acids were used as N-(t-butoxycarbonyl)-O$^\beta$-benzyl-L-aspartic acid anhydride, N-(t-butoxycarbonyl)-S-(p-methoxybenzyl)-L-cysteine anhydride, N-(t-butoxycarbonyl) glycine anhydride, N-(t-butoxycarbonyl)-O$^\gamma$-benzyl-L-glutamic acid anhydride, N-(t-butoxycarbonyl)-L-leucine anhydride, N-(t-butoxycarbonyl)-O-benzyl-L-serine anhydride, N-(t-butoxycarbonyl)-L-proline anhydride, N-(t-butoxycarbonyl)-O$^\beta$-benzyl-L-threonine anhydride and N-(t-butoxycarbonyl)-L-valine anhydride, respectively and their amounts were about five-fold molar amount based on the amount of the substrate. The condensation reaction was carried out at room temperature. The reaction time was varied depending on the kinds of amino acids to be condensed and ranged from 10 to 20 minutes.

TABLE 1

| Operation | Solvent and/or reagent used | Time |
|---|---|---|
| 1. Removal of t-butoxycarbonyl group | trifluoroacetic acid | 5 minutes |
| 2. Washing | N,N-dimethylformamide | 40 seconds |
| 3. Neutralization | N,N-dimethylformamide solution containing 20% by volume of diisopropylethylamine | 1 minute |
| 4. Washing | N,N-dimethylformamide | 40 seconds |
| 5. Condensation reaction | N,N-dimethylformamide solution containing amino acid (10 to 25 ml) | 10 to 20 minutes |
| 6. Washing | dichloromethane | 40 seconds |

After completion of the reaction operation for all the amino acids, the resulting resin was washed on a glass filter with diethyl ether, dichloromethane and methanol in order and vacuum dried to produce 0.41 g of a dried resin. In a reaction vessel made of polytrifluoromonochloroethylene (manufactured by Peptide Kenkyusho Co., Ltd., HF-reaction apparatus, Type I), 0.41 g of the resulting dried resin was admixed with 0.6 ml of anisole and 0.1 ml of ethyl methyl sulfide and to the mixture was added 4 ml of hydrogen fluoride at −20° C. The mixture was stirred at the same temperature for 30 minutes and then at 0° C. for 30 minutes. Hydrogen fluoride, anisole and ethyl methyl sulfide were removed from the resulting reaction mixture under reduced pressure and the residue was thoroughly washed on a glass filter with diethyl ether. The residue was extracted with a 2N aqueous acetic acid solution and the extract was lyophilized to produce a crude product of peptide (0.2 g).

The resulting crude product of peptide was purified by preparative reversed phase high performance liquid chromatography [column: column (inner diameter: 10 mm, length: 300 mm) packed with octadecylated silica gel (grain size: 5 μm), manufactured by Chemco Co., Ltd., Develosil ODS; mobile phase: mixed solvent of acetonitrile containing 0.05% by volume of trifluoroacetic acid and water (the concentration of acetonitrile was gradually changed from 20% by volume to 35% by volume for 20 minutes.)] to obtain 50 mg of the desired purified product of peptide.

The resulting purified product of peptide was subjected to analytical reversed phase high performance liquid chromatography [column: column (inner diameter: 4 mm, length: 150 mm) packed with octadecylated silica gel (grain size: 5 μm), manufactured by Toso Co., Ltd., TSK gel ODS80TM; mobile phase: mixed solvent of acetonitrile containing 0.05% by volume of trifluoroacetic acid and water (the concentration of acetonitrile was gradually changed from 5% by volume to 50% by volume for 30 minutes); flow rate: 1 ml/minute; detection method: absorbance at wavelength of 210 nm] and the result showed a single sharp peak at 17.5 minutes. The molecular weight of the purified product obtained by mass spectrum according to fast atomic bombardment method (hereinafter abbreviated as FAB method) was 2046 (theoretical value: 2045.22). In addition, the purified product was hydrolyzed with hydrochloric acid and the resulting product was subjected to analysis of the amino acid composition. The results are as follows (figures in parentheses mean theoretical value):

lysine: 1.04 (1), aspartic acid: 2.09 (2), glutamic acid: 2.02 (2), proline: 3.10 (3), valine: 1.90 (2), glycine: 1.95 (2), cystine: 0.44 (0.5), threonine: 3.11 (3), leucine: 1.99 (2), serine: 1.98 (2).

EXAMPLES 2 TO 96

According to the same manner as that described in Example 1, the solid phase synthesis of peptide and purification thereof were carried out to obtain the peptides shown in Table 2, Table 3, Table 4, Table 5, Table 6, Table 7, Table 8, Table 9, Table 10, Table 11, Table 12 and Table 13. However, in Example 2, Example 5, Example 42 and Example 45, a granular resin of a styrene-divinylbenzene copolymer [molar ratio of styrene to divinylbenzene being 99:1] containing 4-[N-(t-butoxycarbonyl)-O$^\beta$-benzyl-α-L-aspartyloxymethyl]-phenylacetamidomethyl group in a ratio of 0.78 mmole/g (resin) [manufactured by Applied Biosystems Corp., U.S.A., PAM Aspartic acid, t-Boc-L-Asp (OBzl)] was used as the resin for the solid phase. In Example 3, Example 11, Example 19, Example 27, Example 35, Example 43, Example 51, Example 59, Example 67, Example 75, Example 83 and Example 91, a granular resin of a styrene-divinylbenzene copolymer [molar ratio of styrene to divinylbenzene being 99:1] containing 4-[N-(t-butoxycarbonyl)-O$^\gamma$-benzyl-α-L-glutamyloxymethyl]phenylacetamidomethyl group in a ratio of 0.78 mmole/g (resin) [manufactured by Applied Biosystems Corp., U.S.A., PAM Glutamic acid, t-Boc-L-Glu (OBzl)] was used. In Example 4, Example 12, Example 20, Example 28, Example 36, Example 44, Example 52, Example 60, Example 68, Example 76, Example 84 and Example 92, a granular resin of a styrene-divinylbenzene copolymer [molar ratio of styrene to divinylbenzene being 99:1] containing 4-[N-(t-butoxycarbonyl)glycyloxymethyl]phenylacetamidomethyl group in a ratio of 0.78 mmole/g (resin) [manufactured by Applied Biosystems Corp., U.S.A., PAM Glycine, t-Boc-Gly] was used. In Example 9, Example 10, Example 13, Example 17, Example 25, Example 33, Example 34, Example 37, Example 41, Example 49, Example 57, Example 58, Example 61, Example 65, Example 66, Example 69, Example 73, Example 74, Example 77, Example 81, Example 82, Example 85, Example 89, Example 90 and Example 93; a granular resin of a styrene-divinylbenzene copolymer [molar ratio of styrene to divinylbenzene being 99:1] containing 4-[N$^\alpha$-(t-butoxycarbonyl)-N$^\epsilon$-chlorobenzyloxycarbonyl)-L-lysyloxymethyl]phenylacetamidomethyl group in a ratio of 0.78 mmole/g (resin) [manufactured by Applied Biosystems Corp., U.S.A., PAM Lysine, t-Boc-L-Lys (Cl-Z)] was used. In Example 18, Example 21, Example 50 and Example 53, a granular resin of a styrene-divinylbenzene copolymer [molar ratio of styrene to divinylbenzene being 99:1] containing 4-[N-(t-butoxylcarbonyl)-O-benzyl-L-seryloxymethyl]-phenylacetamidomethyl group in a ratio of 0.78 mmole/g (resin) [manufactured by Applied Biosystems Corp., U.S.A., PAM Serine, t-Boc-L-Ser] was used. In Example 26 and Example 29, a granular resin of a styrene-divinylbenzene copolymer [molar ratio of styrene to divinylbenzene being 99:1] containing 4-[N-(t-butoxylcarbonyl)-L-alanyloxymethyl]-phenylacetamidomethyl group in a ratio of 0.76 mmole/g (resin) [manufactured by Applied Biosystems Corp., U.S.A., PAM Alanine, t-Boc-L-Ala] was used. In Example 6, Example 7, Example 8, Example 14, Example 15, Example 16, Example 22, Example 23, Example 24, Example 30, Example 31, Example 32, Example 38, Example 39, Example 40, Example 46, Example 47, Example 48, Example 54, Example 55, Example 56, Example 62, Example 63, Example 64, Example 70, Example 71, Example 72, Example 78, Example 79, Example 80, Example 86, Example 87, Example 88, Example 94, Example 95 and Example 96, a granular resin of a styrene-divinylbenzene copolymer [molar ratio of styrene to divinylbenzene being 99:1] containing α-amino-p-methylbenzyl group in a ratio of 0.78 mmole/g (resin) [manufactured by Applied Biosystems Corp., U.S.A., p-Methyl BHA Resin] was used. And, in the condensation reaction, L-alanine, L-arginine, L-asparagine, L-glutamine, L-histidine, L-isoleucine, L-lysine, L-phenylalanine, L-tryptophan, L-tyrosine, 12-aminododecanoic acid and 18-aminooctadecanoic acid were used as N-(t-butoxycarbonyl)-L-alanine anhydride, N-(t-butoxycarbonyl)(2,4,6-trimethyl) benzene sulfonyl-L-arginine hydroxybenzotriazyl ester, N-(t-butoxycarbonyl)-L-aspargine hydroxybenzotriazyl ester, N-(t-butoxycarbonyl)-L-glutamine hydroxybenzotriazyl ester, N$^\alpha$-(t-butoxycarbonyl)-N$^{Im}$-dinitrophenyl-L-histidine hydroxybenzotriazyl ester, N-(t-butoxycarbonyl)-L-isoleucine anhydride, N$^\alpha$-(t-butoxycarbonyl)-N$^\epsilon$-2-chlorobenzyloxycarbonyl-L-lysine anhydride, N-(t-butoxycarbonyl)-L-phenylalanine anhydride, N-(t-butoxycarbonyl)-N$^{Im}$-formyl-L-tryptophan anhydride, N-(t-butoxycarbonyl)-O-(p-bromo) benzyloxycarbonyl-L-tyrosine anhydride, 12-(t-butoxycarbonylamino) dodecanoic acid anhydride and 18-(t-butoxycarbonylamino) octadecanoic acid anhydride, respectively.

When the resulting purified products were subjected to analytical reversed phase high performance liquid chromatography [column: column (inner diameter: 4 mm, length: 150 mm) packed with octadecylated silica gel (grain size: 5 μm), manufactured by Toso Co., Ltd., TSK- gel ODS80TM; mobile phase: mixed solvent of acetonitrile containing 0.05% by volume of trifluoroacetic acid and water (the concentration of acetonitrile was gradually changed from 5% by volume to 50% by volume for 30 minutes); flow rate: 1 ml/minute; detection method: absorbance at wavelength of 210 nm], they showed a single sharp peak. The molecular weight of the purified products obtained by mass spectrum according to FAB method and the values of amino acid composition analysis of the products obtained by hydrolysis with hydrochloric acid are shown in Table 14, respectively.

TABLE 2

A: —Thr—Ser—Leu—Pro—Gly—Asp—Ser—Val—Thr—Leu—Thr—Cys—Pro—Gly—Val—Glu—Pro—Glu—Asp—

| Example | X | Y | Z |
|---|---|---|---|
| 2 | —(Lys)$_2$— | — | OH |
| 3 | —NH—(CH$_2$)$_{11}$CO— | —(Glu)$_5$— | OH |
| 4 | —NH—(CH$_2$)$_{17}$CO— | —Gly— | OH |
| 5 | — | — | OH |
| 6 | —Lys— | —Asp— | NH$_2$ |
| 7 | —(Glu)$_5$— | —Lys—Gly— | NH$_2$ |
| 8 | —(Asp)$_5$— | —Ala—Ala—Gly— | NH$_2$ |

TABLE 3

A: —Gly—Thr—Val—His—Leu—Leu—Val—Asp—Val—Pro—Pro—Glu—Glu—Pro—Gln—Leu—Ser—Cys—Phe—Arg—Lys—

| Example | X | Y | Z |
|---|---|---|---|
| 9 | — | —Lys— | OH |
| 10 | —(Lys)$_2$— | — | OH |
| 11 | —NH—(CH$_2$)$_{11}$CO— | —(Glu)$_5$— | OH |
| 12 | —NH—(CH$_2$)$_{17}$CO— | —Gly— | OH |
| 13 | — | — | OH |
| 14 | —Lys— | —Asp— | NH$_2$ |
| 15 | —(Glu)$_5$— | —Lys—Gly— | NH$_2$ |
| 16 | —(Asp)$_5$— | —Ala—Ala—Gly— | NH$_2$ |

TABLE 4

A: —Arg—Lys—Phe—Gln—Asn—Ser—Pro—Ala—Glu—Asp—Phe—Gln—Glu—Pro—Cys—Gln—Tyr—Ser—Gln—Glu—Ser—

| Example | X | Y | Z |
|---|---|---|---|
| 17 | — | —Lys— | OH |
| 18 | —(Lys)$_2$— | — | OH |
| 19 | —NH—(CH$_2$)$_{11}$CO— | —(Glu)$_5$— | OH |
| 20 | —NH—(CH$_2$)$_{17}$CO— | —Gly— | OH |
| 21 | — | — | OH |
| 22 | —Lys— | —Asp— | NH$_2$ |
| 23 | —(Glu)$_5$— | —Lys—Gly— | NH$_2$ |
| 24 | —(Asp)$_5$— | —Ala—Ala—Gly— | NH$_2$ |

TABLE 5

A: —Gln—Ala—Leu—Thr—Thr—Asn—Lys—Asp—Asp—Asp—Asn—Ile—Leu—Phe—Arg—Asp—Ser—Ala—

| Example | X | Y | Z |
|---|---|---|---|
| 25 | — | —Lys— | OH |
| 26 | —(Lys)$_2$— | — | OH |
| 27 | —NH—(CH$_2$)$_{11}$CO— | —(Glu)$_5$— | OH |
| 28 | —NH—(CH$_2$)$_{17}$CO— | —Gly— | OH |
| 29 | — | — | OH |
| 30 | —Lys— | —Asp— | NH$_2$ |
| 31 | —(Glu)$_5$— | —Lys—Gly— | NH$_2$ |
| 32 | —(Asp)$_5$— | —Ala—Ala—Gly— | NH$_2$ |

TABLE 6

A: —Trp—Asn—Ser—Ser—Phe—Tyr—Arg—Leu—Arg—Phe—Glu—Leu—Arg—Tyr—Arg—Ala—Glu—Arg—Ser—Lys—

| Example | X | Y | Z |
|---|---|---|---|
| 33 | — | —Lys— | OH |
| 34 | —(Lys)$_2$— | — | OH |
| 35 | —NH—(CH$_2$)$_{11}$CO— | —(Glu)$_5$— | OH |
| 36 | —NH—(CH$_2$)$_{17}$CO— | —Gly— | OH |
| 37 | — | — | OH |
| 38 | —Lys— | —Asp— | NH$_2$ |
| 39 | —(Glu)$_5$— | —Lys—Gly— | NH$_2$ |
| 40 | —(Asp)$_5$— | —Ala—Ala—Gly— | NH$_2$ |

TABLE 7

A: —Ser—Thr—Pro—Ser—Leu—Thr—Thr—Lys—Ala—Val—Leu—Leu—Val—Arg—Lys—Phe—Glu—Asn—Ser—Pro—Ala—Glu—Asp—

| Example | X | Y | Z |
|---|---|---|---|
| 41 | — | —Lys— | OH |
| 42 | —(Lys)$_2$— | — | OH |
| 43 | —NH—(CH$_2$)$_{11}$CO— | —(Glu)$_5$— | OH |
| 44 | —NH—(CH$_2$)$_{17}$CO— | —Gly— | OH |
| 45 | — | — | OH |
| 46 | —Lys— | —Asp— | NH$_2$ |
| 47 | —(Glu)$_5$— | —Lys—Gly— | NH$_2$ |
| 48 | —(Asp)$_5$— | —Ala—Ala—Gly— | NH$_2$ |

TABLE 8

A: —Asn—Pro—Arg—Trp—Leu—Ser—Val—Thr—Trp—Gln—Asp—Pro—His—Ser—

| Example | X | Y | Z |
|---|---|---|---|
| 49 | — | —Lys— | OH |
| 50 | —(Lys)$_2$— | — | OH |
| 51 | —NH—(CH$_2$)$_{11}$CO— | —(Glu)$_5$— | OH |
| 52 | —NH—(CH$_2$)$_{17}$CO— | —Gly— | OH |
| 53 | — | — | OH |
| 54 | —Lys— | —Asp— | NH$_2$ |
| 55 | —(Glu)$_5$— | —Lys—Gly— | NH$_2$ |
| 56 | —(Asp)$_5$— | —Ala—Ala—Gly— | NH$_2$ |

TABLE 9

A: —His—Ser—Trp—Asn—Ser—Ser—Phe—Tyr—Arg—Leu—Arg—Phe—Glu—Leu—Arg—Tyr—Arg—Ala—Glu—Arg—Ser—Lys—

| Example | X | Y | Z |
|---|---|---|---|
| 57 | — | —Lys— | OH |
| 58 | —(Lys)$_2$— | — | OH |
| 59 | —NH—(CH$_2$)$_{11}$CO— | —(Glu)$_5$— | OH |
| 60 | —NH—(CH$_2$)$_{17}$CO— | —Gly— | OH |
| 61 | — | — | OH |
| 62 | —Lys— | —Asp— | NH$_2$ |
| 63 | —(Glu)$_5$— | —Lys—Gly— | NH$_2$ |
| 64 | —(Asp)$_5$— | —Ala—Ala—Gly— | NH$_2$ |

TABLE 10

A: —Pro—His—Ser—Trp—Asn—Ser—Ser—Phe—Tyr—Arg—Leu—Arg—Phe—Glu—Leu—Arg—Tyr—Arg—Ala—Glu—Arg—Ser—Lys—

| Example | X | Y | Z |
|---|---|---|---|
| 65 | — | —Lys— | OH |
| 66 | —(Lys)$_2$— | — | OH |
| 67 | —NH—(CH$_2$)$_{11}$CO— | —(Glu)$_5$— | OH |
| 68 | —NH—(CH$_2$)$_{17}$CO— | —Gly— | OH |
| 69 | — | — | OH |
| 70 | —Lys— | —Asp— | NH$_2$ |
| 71 | —(Glu)$_5$— | —Lys—Gly— | NH$_2$ |

TABLE 10-continued

A: —Pro—His—Ser—Trp—Asn—Ser—Ser—Phe—Tyr—Arg—Leu—Arg—Phe—Glu—Leu—Arg—Tyr—Arg—Ala—Glu—Arg—Ser—Lys—

| Example | X | Y | Z |
|---------|---|---|---|
| 72 | —(Asp)$_5$— | —Ala—Ala—Gly— | NH$_2$ |

TABLE 11

A: —Asp—Pro—His—Ser—Trp—Asn—Ser—Ser—Phe—Tyr—Arg—Leu—Arg—Phe—Glu—Leu—Arg—Tyr—Arg—Ala—Glu—Arg—Ser—Lys—

| Example | X | Y | Z |
|---------|---|---|---|
| 73 | — | —Lys— | OH |
| 74 | —(Lys)$_2$— | — | OH |
| 75 | —NH—(CH$_2$)$_{11}$CO— | —(Glu)$_5$— | OH |
| 76 | —NH—(CH$_2$)$_{17}$CO— | —Gly— | OH |
| 77 | — | — | OH |
| 78 | —Lys— | —Asp— | NH$_2$ |
| 79 | —(Glu)$_5$— | —Lys—Gly— | NH$_2$ |
| 80 | —(Asp)$_5$— | —Ala—Ala—Gly— | NH$_2$ |

TABLE 12

A: —Gln—Asp—Pro—His—Ser—Trp—Asn—Ser—Ser—Phe—Tyr—Arg—Leu—Arg—Phe—Glu—Leu—Arg—Tyr—Arg—Ala—Glu—Arg—Ser—Lys—

| Example | X | Y | Z |
|---------|---|---|---|
| 81 | — | —Lys— | OH |
| 82 | —(Lys)$_2$— | — | OH |
| 83 | —NH—(CH$_2$)$_{11}$CO— | —(Glu)$_5$— | OH |
| 84 | —NH—(CH$_2$)$_{17}$CO— | —Gly— | OH |
| 85 | — | — | OH |
| 86 | —Lys— | —Asp— | NH$_2$ |
| 87 | —(Glu)$_5$— | —Lys—Gly— | NH$_2$ |
| 88 | —(Asp)$_5$— | —Ala—Ala—Gly— | NH$_2$ |

TABLE 13

A: —Trp—Gln—Asp—Pro—His—Ser—Trp—Asn—Ser—Ser—Phe—Tyr—Arg—Leu—Arg—Phe—Glu—Leu—Arg—Tyr—Arg—Ala—Glu—Arg—Ser—Lys—

| Example | X | Y | Z |
|---------|---|---|---|
| 89 | — | —Lys— | OH |
| 90 | —(Lys)$_2$— | — | OH |
| 91 | —NH—(CH$_2$)$_{11}$CO— | —(Glu)$_5$— | OH |
| 92 | —NH—(CH$_2$)$_{17}$CO— | —Gly— | OH |
| 93 | — | — | OH |
| 94 | —Lys— | —Asp— | NH$_2$ |
| 95 | —(Glu)$_5$— | —Lys—Gly— | NH$_2$ |
| 96 | —(Asp)$_5$— | —Ala—Ala—Gly— | NH$_2$ |

TABLE 14

| | \multicolumn{8}{c}{Example} | | | | | | | |
|---|---|---|---|---|---|---|---|---|
| | 2 | 3 | 4 | 5 | 6 | 7 | 8 | 9 |
| Molecular weight by FAB method mass spectrum | 2172 (2173.39) | 2760 (2759.93) | 2255 (2255.56) | 1916 (1917.05) | 2158 (2159.31) | 2489 (2489.616) | 2690 (2690.70) | 2491 (2492.88) |
| amino acid composition analysis | | | | | | | | |
| Alanine | — | — | — | — | — | — | 1.98 (2) | — |
| Arginine | — | — | — | — | — | — | — | 0.98 (1) |
| Asparagine | — | — | — | — | — | — | — | — |
| Aspartic acid | 2.08 (2) | 2.07 (2) | 2.05 (2) | 2.06 (2) | 3.10 (3) | 2.06 (2) | 7.21 (7) | 1.02 (1) |
| Cystine | 0.43 (0.5) | 0.45 (0.5) | 0.42 (0.5) | 0.44 (0.5) | 0.43 (0.5) | 0.42 (0.5) | 0.43 (0.5) | 0.40 (0.5) |
| Glutamine | — | — | — | — | — | — | — | 0.90 (1) |
| Glutamic acid | 2.03 (2) | 7.22 (7) | 2.04 (2) | 2.02 (2) | 2.03 (2) | 5.10 (5) | 2.03 (2) | 2.04 (2) |
| Glycine | 1.96 (2) | 1.96 (2) | 2.92 (3) | 1.97 (2) | 1.98 (2) | 2.95 (3) | 2.98 (3) | 0.99 (1) |
| Histidine | — | — | — | — | — | — | — | 0.98 (1) |
| Isoleucine | — | — | — | — | — | — | — | — |
| Leucine | 1.98 (2) | 1.97 (2) | 1.98 (2) | 1.97 (2) | 1.98 (2) | 1.97 (2) | 1.98 (2) | 2.97 (3) |
| Lysine | 2.07 (2) | — | — | — | 1.02 (1) | 1.01 (1) | — | 2.03 (2) |
| Phenylalanine | — | — | — | — | — | — | — | 1.01 (1) |
| Proline | 3.12 (3) | 3.11 (3) | 3.10 (3) | 3.10 (3) | 3.09 (3) | 3.08 (3) | 3.09 (3) | 3.06 (3) |
| Serine | 1.97 (2) | 1.96 (2) | 1.96 (2) | 1.98 (2) | 1.97 (2) | 1.98 (2) | 1.97 (2) | 0.98 (1) |
| Threonine | 3.12 (3) | 3.11 (3) | 3.11 (3) | 3.10 (3) | 3.12 (3) | 3.09 (3) | 3.09 (3) | 1.03 (1) |
| Tyrosine | — | — | — | — | — | — | — | — |
| Valine | 1.92 (2) | 1.93 (2) | 1.94 (2) | 1.96 (2) | 1.94 (2) | 1.98 (2) | 1.98 (2) | 2.90 (3) |
| $H_2N{-}(CH_2)_7{-}COOH$ | — | 1.01 (1) | — | — | — | — | — | — |
| $H_2N{-}(CH_2)_7{-}COOH$ | — | — | 1.02 (1) | — | — | — | — | — |
| Valine | — | 0.97 (1) | 0.98 (1) | 0.99 (1) | 0.97 (1) | 0.99 (1) | 0.99 (1) | — |

| | Example | | | | | | | |
|---|---|---|---|---|---|---|---|---|
| | 10 | 11 | 12 | 13 | 14 | 15 | 16 | 17 |
| Molecular weight by FAB method mass spectrum | 2620 (2621.06) | 3207 (3207.59) | 2702 (2703.23) | 2364 (2364.71) | 2606 (2606.97) | 2936 (2937.28) | 3138 (3138.36) | 2646 (2646.80) |
| amino acid composition analysis | | | | | | | | |
| Alanine | — | — | — | — | — | — | 1.97 (2) | 1.01 (1) |
| Arginine | 0.96 (1) | 0.97 (1) | 0.96 (1) | 0.98 (1) | 0.98 (1) | 0.96 (1) | 0.97 (1) | 0.96 (1) |
| Asparagine | — | — | — | — | — | — | — | 0.92 (1) |
| Aspartic acid | 1.01 (1) | 1.02 (1) | 1.03 (1) | 1.01 (1) | 2.02 (2) | 1.01 (1) | 6.17 (6) | 1.01 (1) |
| Cystine | 0.42 (0.5) | 0.43 (0.5) | 0.43 (0.5) | 0.40 (0.5) | 0.44 (0.5) | 0.40 (0.5) | 0.42 (0.5) | 0.44 (0.5) |
| Glutamine | 0.88 (1) | 0.89 (1) | 0.90 (1) | 0.90 (1) | 0.91 (1) | 0.89 (1) | 0.91 (1) | 3.75 (4) |
| Glutamic acid | 2.03 (2) | 7.20 (7) | 2.02 (2) | 2.04 (2) | 2.03 (2) | 5.09 (5) | 2.03 (2) | 3.01 (3) |
| Glycine | 0.98 (1) | 0.99 (1) | 1.99 (2) | 0.98 (1) | 0.99 (1) | 1.98 (2) | 1.96 (2) | — |
| Histidine | 0.98 (1) | 0.97 (1) | 0.98 (1) | 0.98 (1) | 0.99 (1) | 0.99 (1) | 0.97 (1) | — |
| Isoleucine | — | — | — | — | — | — | — | — |
| Leucine | 2.96 (3) | 2.95 (3) | 2.96 (3) | 2.94 (3) | 2.92 (3) | 2.95 (3) | 2.96 (3) | — |
| Lysine | 2.05 (2) | 1.02 (1) | 1.01 (1) | 1.01 (1) | 2.02 (2) | 2.03 (2) | 1.02 (1) | 2.02 (2) |
| Phenylalanine | 1.02 (1) | 1.02 (1) | 1.02 (1) | 1.02 (1) | 1.02 (1) | 1.01 (1) | 1.03 (1) | 2.02 (2) |
| Proline | 3.07 (3) | 3.10 (3) | 3.08 (3) | 3.12 (3) | 3.10 (3) | 3.08 (3) | 3.10 (3) | 2.05 (2) |
| Serine | 0.99 (1) | 0.97 (1) | 0.98 (1) | 0.97 (1) | 0.97 (1) | 1.03 (1) | 0.98 (1) | 2.97 (3) |
| Threonine | 1.02 (1) | 1.03 (1) | 1.01 (1) | 1.02 (1) | 1.01 (1) | 1.03 (1) | 1.03 (1) | — |
| Tyrosine | — | 2.97 (3) | — | — | — | — | — | — |
| Valine | 2.92 (3) | — | 2.92 (3) | 2.95 (3) | 2.95 (3) | 2.96 (3) | 2.96 (3) | 0.98 (1) |
| $H_2N{-}(CH_2)_7{-}COOH$ | — | 0.99 (1) | 1.00 (1) | — | — | — | — | — |
| $H_2N{-}(CH_2)_7{-}COOH$ | — | — | — | — | — | — | — | — |

| | Example | | | | | | | |
|---|---|---|---|---|---|---|---|---|
| | 18 | 19 | 20 | 21 | 22 | 23 | 24 | 25 |
| Molecular weight by FAB method mass spectrum | 2774 (2774.97) | 3360 (3361.50) | 2856 (2857.14) | 2518 (2518.63) | 2760 (2760.89) | 3090 (3091.19) | 3291 (3292.28) | 2165 (2165.32) |
| amino acid composition analysis | | | | | | | | |
| Alanine | 1.02 (1) | 1.01 (1) | 1.01 (1) | 1.00 (1) | 0.99 (1) | 1.01 (1) | 2.95 (3) | 2.02 (2) |
| Arginine | 0.95 (1) | 0.94 (1) | 0.95 (1) | 0.94 (1) | 0.92 (1) | 0.95 (1) | 0.95 (1) | 0.96 (1) |
| Asparagine | 0.90 (1) | 0.89 (1) | 0.90 (1) | 0.90 (1) | 0.89 (1) | 0.91 (1) | 0.92 (1) | 1.87 (2) |
| Aspartic acid | 1.00 (1) | 1.02 (1) | 1.01 (1) | 1.00 (1) | 1.98 (2) | 1.01 (1) | — | 3.99 (4) |
| Cystine | 0.44 (0.5) | 0.43 (0.5) | 0.42 (0.5) | 0.44 (0.5) | 0.40 (0.5) | 0.44 (0.5) | 6.18 (6) | — |
| Glutamine | 3.79 (4) | 3.72 (4) | 3.80 (4) | 3.82 (4) | 3.74 (4) | 3.85 (4) | 0.44 (0.5) | 0.95 (1) |
| Glutamic acid | 3.03 (3) | 8.21 (8) | 3.02 (3) | 3.05 (3) | 3.01 (3) | 6.10 (6) | 3.84 (4) | — |
| Glycine | — | — | 1.00 (1) | — | — | 0.99 (1) | 3.06 (3) | — |
| Histidine | — | — | — | — | — | — | 0.98 (1) | — |
| Isoleucine | — | — | — | — | — | — | — | — |
| Leucine | 3.04 (3) | 1.01 (1) | 1.02 (1) | 1.01 (1) | 2.01 (2) | 2.02 (2) | — | 1.01 (1) |
| Lysine | 2.03 (2) | 2.03 (2) | 2.02 (2) | 2.04 (2) | 2.02 (2) | 2.03 (2) | 1.01 (1) | 1.98 (2) |
| Phenylalanine | 2.06 (2) | 2.05 (2) | 2.03 (2) | 2.03 (2) | 2.01 (2) | 2.03 (2) | 2.02 (2) | 2.04 (2) |
| Proline | 2.97 (3) | 2.95 (3) | 2.96 (3) | 2.95 (3) | 2.90 (3) | 2.93 (3) | 2.97 (3) | 1.01 (1) |
| Serine | — | — | — | — | — | — | — | 0.98 (1) |
| Threonine | — | — | — | — | — | — | — | 2.03 (2) |
| Tyrosine | 0.97 (1) | 0.97 (1) | 0.98 (1) | 0.99 (1) | 0.97 (1) | 0.99 (1) | 0.99 (1) | — |
| Tryptophan | — | — | — | — | — | — | — | — |
| Valine | — | — | — | — | — | — | — | — |

| | Example | | | | | | | |
|---|---|---|---|---|---|---|---|---|
| | 26 | 27 | 28 | 29 | 30 | 31 | 32 | 33 |
| Molecular weight by FAB method mass spectrum | 2293 (2293.50) | 2880 (2880.03) | 2376 (2375.67) | 2037 (2037.15) | 2279 (2279.41) | 2610 (2609.72) | 2811 (2810.80) | 2793 (2793.15) |
| amino acid composition analysis | | | | | | | | |
| Alanine | 2.03 (2) | 2.03 (2) | 2.02 (2) | 2.03 (2) | 2.02 (2) | 2.02 (2) | 4.07 (4) | 1.01 (1) |
| Arginine | 0.96 (1) | 0.97 (1) | 0.97 (1) | 0.96 (1) | 0.96 (1) | 0.94 (1) | 0.97 (1) | 4.83 (5) |
| Asparagine | 1.85 (2) | 1.86 (2) | 1.85 (2) | 1.82 (2) | 1.84 (2) | 1.84 (2) | 1.83 (2) | 0.91 (1) |
| Aspartic acid | 3.95 (4) | 3.94 (4) | 3.96 (4) | 3.95 (4) | 4.90 (5) | 3.92 (4) | 8.89 (9) | — |
| Cystine | — | — | — | — | — | — | — | — |
| Glutamine | 0.92 (1) | 0.91 (1) | 0.92 (1) | 0.90 (1) | 0.92 (1) | 0.91 (1) | 0.91 (1) | 2.02 (2) |
| Glutamic acid | — | 5.06 (5) | — | — | — | 3.05 (5) | — | — |
| Glycine | — | — | 0.99 (1) | — | — | 0.99 (1) | 0.98 (1) | — |
| Histidine | — | — | — | — | — | — | — | — |
| Isoleucine | 0.99 (1) | 0.98 (1) | 0.99 (1) | 1.01 (1) | 1.02 (1) | 1.02 (1) | 1.01 (1) | 1.99 (2) |
| Leucine | 1.97 (2) | 1.98 (2) | 1.97 (2) | 1.96 (2) | 1.95 (2) | 1.97 (2) | 1.96 (2) | 2.07 (2) |
| Lysine | 3.06 (3) | 1.01 (1) | 1.01 (1) | 1.01 (1) | 2.02 (2) | 2.01 (2) | 1.01 (1) | 2.02 (2) |
| Phenylalanine | 1.00 (1) | 1.03 (1) | 1.01 (1) | 1.03 (1) | 1.01 (1) | 1.02 (1) | 1.01 (1) | — |
| Proline | 0.97 (1) | 0.96 (1) | 0.98 (1) | 0.99 (1) | 0.98 (1) | 0.98 (1) | 0.97 (1) | 2.99 (3) |
| Serine | 2.02 (2) | 2.03 (2) | 2.02 (2) | 2.02 (2) | 2.01 (2) | 2.01 (2) | 2.03 (2) | 1.97 (2) |
| Threonine | — | — | — | — | — | — | — | 1.01 (1) |
| Tyrosine | — | — | — | — | — | — | — | — |

TABLE 14-continued

| | 34 | 35 | 36 | 37 | 38 | 39 | 40 | Example 41 | 42 | 43 | 44 | 45 | 46 | 47 | 48 | 49 |
|---|---|---|---|---|---|---|---|---|---|---|---|---|---|---|---|---|
| $H_2N\text{-}(CH_2)_nCOOH$ | — | 1.01 (1) | — | — | — | — | — | — | — | 0.98 (1) | — | — | — | — | — | — |
| $H_2N\text{-}(CH_2)_nCOOH$ | — | — | 0.99 (1) | — | — | — | — | — | — | — | 0.99 (1) | — | — | — | — | — |
| Molecular weight by FAB method mass spectrum | 2921 (2921.32) | 3508 (3507.72) | 3003 (3003.30) | 2665 (2664.97) | 2907 (2907.25) | 3237 (3236.56) | 3439 (3438.64) | 2631 (2630.99) | 2759 (2759.16) | 3345 (3345.57) | 2841 (2841.14) | 2503 (2502.52) | 2744 (2745.10) | 3074 (3074.41) | 3276 (3276.49) | 1851 (1851.03) |
| amino acid composition analysis | | | | | | | | | | | | | | | | |
| Alanine | 0.98 (1) | 0.99 (1) | 0.99 (1) | 0.98 (1) | 0.97 (1) | 0.99 (1) | 2.97 (3) | 1.96 (2) | 1.97 (2) | 1.98 (2) | 1.98 (2) | 1.97 (2) | 1.96 (2) | 1.98 (2) | 3.92 (4) | — |
| Arginine | 4.89 (5) | 4.86 (5) | 4.90 (5) | 4.86 (5) | 4.91 (5) | 4.88 (5) | 4.89 (5) | 0.98 (1) | 0.96 (1) | 0.97 (1) | 0.96 (1) | 0.98 (1) | 0.98 (1) | 0.96 (1) | 0.97 (1) | 0.96 (1) |
| Asparagine | 0.93 (1) | 0.92 (1) | 0.90 (1) | 0.91 (1) | 0.92 (1) | 0.93 (1) | 0.90 (1) | 0.92 (1) | 0.90 (1) | 0.91 (1) | 0.90 (1) | 0.91 (1) | 0.93 (1) | 0.90 (1) | 0.92 (1) | 0.91 (1) |
| Aspartic acid | — | — | — | — | 1.02 (1) | — | 5.13 (5) | 1.02 (1) | 1.01 (1) | 1.02 (1) | 1.03 (1) | 1.01 (1) | 2.02 (2) | 1.01 (1) | 6.17 (6) | 1.01 (1) |
| Cystine | — | — | — | — | — | — | — | — | — | — | — | — | — | — | — | — |
| Glutamine | — | — | — | — | — | — | — | 0.90 (1) | 0.88 (1) | 0.89 (1) | 0.90 (1) | 0.90 (1) | 0.91 (1) | 0.89 (1) | 0.91 (1) | 0.90 (1) |
| Glutamic acid | 2.03 (2) | 7.22 (7) | 2.04 (2) | 2.02 (2) | 2.03 (2) | 5.10 (5) | 2.03 (2) | 1.04 (1) | 1.04 (1) | 6.12 (6) | 1.03 (1) | 1.03 (1) | 1.02 (1) | 4.08 (4) | 1.02 (1) | — |
| Glycine | — | — | 0.97 (1) | — | — | 0.98 (1) | 0.98 (1) | — | — | — | 0.99 (1) | — | — | 0.98 (1) | 0.99 (1) | — |
| Histidine | — | — | — | — | — | — | 1.02 (1) | — | — | — | — | — | — | — | — | 0.98 (1) |
| Isoleucine | 1.98 (2) | 1.97 (2) | 1.98 (2) | 1.97 (2) | 1.98 (2) | 1.97 (2) | 1.98 (2) | 2.97 (3) | 2.96 (3) | 2.95 (3) | 2.96 (3) | 2.94 (3) | 2.92 (3) | 2.95 (3) | 2.96 (3) | — |
| Leucine | 3.11 (3) | 1.02 (1) | 1.02 (1) | 1.03 (1) | 2.05 (2) | 2.04 (2) | 1.01 (1) | 3.01 (3) | 4.03 (4) | 2.01 (2) | 2.03 (2) | 2.02 (2) | 3.02 (3) | 3.04 (3) | 2.03 (2) | 1.01 (1) |
| Lysine | — | 2.03 (2) | 2.01 (2) | 2.01 (2) | 2.01 (2) | 2.02 (2) | 2.03 (2) | 1.01 (1) | 1.02 (1) | 1.02 (1) | 1.02 (1) | 1.02 (1) | 1.02 (1) | 1.01 (1) | 1.03 (1) | — |
| Phenylalanine | 2.03 (2) | — | — | — | — | — | — | 2.02 (2) | 2.04 (2) | 2.01 (2) | 2.03 (2) | 2.03 (2) | 2.02 (2) | 2.03 (2) | 2.03 (2) | 2.05 (2) |
| Proline | — | — | — | — | — | — | — | 2.98 (3) | 2.99 (3) | 2.97 (3) | 2.95 (3) | 2.96 (3) | 2.97 (3) | 2.96 (3) | 2.98 (3) | 1.97 (2) |
| Serine | 2.97 (3) | 2.96 (3) | 2.96 (3) | 2.98 (3) | 2.97 (3) | 2.98 (3) | 2.97 (3) | 3.05 (3) | 3.09 (3) | 3.03 (3) | 3.03 (3) | 3.06 (3) | 3.05 (3) | 3.09 (3) | 3.05 (3) | — |
| Threonine | 1.95 (2) | 1.94 (2) | 1.95 (2) | 1.97 (2) | 1.94 (2) | 1.96 (2) | 1.96 (2) | — | — | — | — | — | — | — | — | — |
| Tyrosine | 1.02 (1) | 1.02 (1) | 1.01 (1) | 1.02 (1) | — | — | — | — | — | — | — | — | — | — | — | 2.01 (2) |
| Tryptophan | — | — | — | — | — | — | — | — | — | — | — | — | — | — | — | — |
| Valine | — | — | — | — | — | — | 1.99 (2) | 1.99 (2) | 1.97 (2) | 1.98 (2) | 1.98 (2) | 2.00 (2) | 1.99 (2) | 1.98 (2) | 1.99 (2) | 0.97 (1) |
| $H_2N\text{-}(CH_2)_nCOOH$ | — | 1.01 (1) | — | — | — | — | — | — | — | 0.99 (1) | — | — | — | — | — | — |
| $H_2N\text{-}(CH_2)_nCOOH$ | — | — | 1.02 (1) | — | — | — | — | — | — | — | 1.00 (1) | — | — | — | — | — |

| | 50 | 51 | 52 | 53 | 54 | 55 | 56 | Example 57 | 58 | 59 | 60 | 61 | 62 | 63 | 64 | 65 |
|---|---|---|---|---|---|---|---|---|---|---|---|---|---|---|---|---|
| Molecular weight by FAB method mass spectrum | 1979 (1979.20) | 2566 (2565.61) | 2061 (2061.18) | 1723 (1722.86) | 1965 (1965.14) | 2294 (2294.44) | 2497 (2496.52) | 3017 (3017.36) | 3146 (3145.53) | 3732 (3731.94) | 3228 (3227.51) | 2890 (2889.19) | 3131 (3131.47) | 3461 (3460.77) | 3663 (3662.85) | 3114 (3114.47) |
| amino acid composition analysis | | | | | | | | | | | | | | | | |
| Alanine | 0.95 (1) | 0.94 (1) | 0.95 (1) | 0.94 (1) | 0.92 (1) | 0.95 (1) | 2.01 (2) | 0.98 (1) | 1.00 (1) | 0.99 (1) | 0.99 (1) | 0.97 (1) | 1.00 (1) | 0.99 (1) | 2.97 (3) | 1.00 (1) |
| Arginine | 1.90 (1) | 0.89 (1) | 0.90 (1) | 0.90 (1) | 0.89 (1) | 0.91 (1) | 0.95 (1) | 4.79 (5) | 4.82 (5) | 4.77 (5) | 4.75 (5) | 4.77 (5) | 4.78 (5) | 4.80 (5) | 4.80 (5) | 4.77 (5) |
| Asparagine | 1.00 (1) | 1.02 (1) | 1.01 (1) | 1.00 (1) | 1.98 (2) | 1.01 (1) | 0.92 (1) | 0.90 (1) | 0.91 (1) | 0.90 (1) | 0.88 (1) | 0.87 (1) | 0.92 (1) | 0.91 (1) | 0.93 (1) | 0.89 (1) |
| Aspartic acid | — | — | — | — | — | — | 6.18 (6) | — | — | — | — | — | 1.01 (1) | — | 5.18 (5) | — |
| Cystine | — | — | — | — | — | — | — | — | — | — | — | — | — | — | — | — |
| Glutamine | 0.92 (1) | 0.94 (1) | 0.95 (1) | 0.96 (1) | 0.95 (1) | 0.96 (1) | 0.96 (1) | — | — | — | — | — | — | — | — | — |
| Glutamic acid | — | 5.21 (5) | — | — | — | 3.10 (3) | — | 2.03 (2) | 2.02 (2) | 7.12 (7) | 2.05 (2) | 2.03 (2) | 2.03 (2) | 5.08 (5) | 2.03 (2) | 2.02 (2) |
| Glycine | — | — | 1.00 (1) | — | — | 0.99 (1) | 0.98 (1) | — | — | — | 0.99 (1) | — | — | 0.99 (1) | 1.00 (1) | — |
| Histidine | 0.98 (1) | 0.99 (1) | 0.99 (1) | 0.99 (1) | 0.98 (1) | 0.97 (1) | 0.99 (1) | 0.99 (1) | 0.99 (1) | 1.00 (1) | 0.97 (1) | 0.98 (1) | 0.98 (1) | 0.97 (1) | 0.99 (1) | 1.00 (1) |
| Isoleucine | — | — | — | — | — | — | — | — | — | — | — | — | — | — | — | — |
| Leucine | — | — | — | — | 1.00 (1) | 1.02 (1) | — | 1.98 (2) | 1.97 (2) | 1.96 (2) | 1.97 (2) | 1.97 (2) | 1.96 (2) | 1.96 (2) | 1.97 (2) | 1.97 (2) |
| Lysine | 2.03 (2) | — | — | — | — | — | — | 2.03 (2) | 3.04 (3) | 1.02 (1) | 1.01 (1) | 1.00 (1) | 2.02 (2) | 2.01 (2) | 1.03 (1) | 2.03 (2) |
| Phenylalanine | — | — | — | — | — | — | 2.02 (2) | 2.03 (2) | 2.01 (2) | 2.04 (2) | 2.02 (2) | 2.03 (2) | 2.03 (2) | 2.04 (2) | 2.04 (2) | 2.02 (2) |
| Proline | 2.06 (2) | 2.05 (2) | 2.03 (2) | 2.03 (2) | 2.01 (2) | 2.03 (2) | 1.97 (2) | — | — | — | — | — | — | — | — | 1.01 (1) |
| Serine | 1.98 (2) | 1.95 (2) | 1.97 (2) | 1.95 (2) | 1.97 (2) | 1.96 (2) | — | 3.94 (4) | 3.92 (4) | 3.93 (4) | 3.91 (4) | 3.92 (4) | 3.92 (4) | 3.92 (4) | 3.92 (4) | 3.93 (4) |

TABLE 14-continued

| | 66 | 67 | 68 | 69 | 70 | 71 | 72 | 73 | 74 | 75 | 76 | 77 | 78 | 79 | 80 | 81 |
|---|---|---|---|---|---|---|---|---|---|---|---|---|---|---|---|---|
| | | | | | | | | | Example | | | | | | | |
| Threonine | — | — | — | — | — | — | — | — | — | — | — | — | — | — | — | — |
| Tyrosine | 2.03 (2) | 2.03 (2) | 2.03 (2) | 2.02 (2) | 2.01 (2) | 2.01 (2) | 2.03 (2) | 1.97 (2) | 1.96 (2) | 1.98 (2) | 1.97 (2) | 1.97 (2) | 1.98 (2) | 1.97 (2) | 1.97 (2) | 1.96 (2) |
| Tryptophan | 0.98 (1) | 0.98 (1) | 0.98 (1) | 0.99 (1) | 0.99 (1) | 0.97 (1) | 0.99 (1) | 1.02 (1) | 1.00 (1) | 1.03 (1) | 1.02 (1) | 1.03 (1) | 1.02 (1) | 1.03 (1) | 1.02 (1) | 1.01 (1) |
| Valine | — | 1.01 (1) | — | — | — | — | — | — | — | 0.97 (1) | — | — | — | — | — | — |
| H$_2$N—(CH$_2$)$_7$COOH | — | — | 0.99 (1) | — | — | — | — | — | — | — | 0.96 (1) | — | — | — | — | — |
| H$_2$N—(CH$_2$)$_7$COOH | — | — | — | — | — | — | — | — | — | — | — | — | — | — | — | — |
| Molecular weight by FAB method mass spectrum | 3243 (3242.64) | 3830 (3829.05) | 3324 (3324.62) | 2986 (2986.30) | 3229 (3228.58) | 3559 (3557.88) | 3760 (3759.96) | 3230 (3229.56) | 3358 (3357.73) | 3945 (3944.14) | 3439 (3439.71) | 3101 (3101.39) | 3345 (3343.67) | 3673 (3672.97) | 3876 (3875.05) | 3359 (3357.69) |
| amino acid composition analysis | | | | | | | | | | | | | | | | |
| Alanine | 0.98 (1) | 1.00 (1) | 0.97 (1) | 1.01 (1) | 0.98 (1) | 0.98 (1) | 2.95 (3) | 1.01 (1) | 1.00 (1) | 1.00 (1) | 0.98 (1) | 0.99 (1) | 1.00 (1) | 1.00 (1) | 2.94 (3) | 0.98 (1) |
| Arginine | 4.75 (5) | 4.83 (5) | 4.70 (5) | 4.73 (5) | 4.75 (5) | 4.72 (5) | 4.80 (5) | 4.71 (5) | 4.72 (5) | 4.75 (5) | 4.73 (5) | 4.80 (5) | 4.70 (5) | 4.71 (5) | 4.76 (5) | 4.79 (5) |
| Asparagine | 0.91 (1) | 0.92 (1) | 0.92 (1) | 0.91 (1) | 0.92 (1) | 0.90 (1) | 0.90 (1) | 0.91 (1) | 0.92 (1) | 0.93 (1) | 0.91 (1) | 0.91 (1) | 0.93 (1) | 0.92 (1) | 0.91 (1) | 0.91 (1) |
| Aspartic acid | — | — | — | — | 1.02 (1) | — | 5.09 (5) | 1.00 (1) | 1.01 (1) | 1.01 (1) | 1.01 (1) | 1.00 (1) | 2.03 (2) | 1.01 (1) | 6.08 (6) | 0.99 (1) |
| Cystine | — | — | — | — | — | — | — | — | — | — | — | — | — | — | — | — |
| Glutamine | — | — | — | — | — | — | — | — | — | — | — | — | — | — | — | 0.94 (1) |
| Glutamic acid | 2.03 (2) | 7.20 (7) | 2.04 (2) | 2.03 (2) | 2.04 (2) | 5.12 (5) | 2.05 (2) | 2.04 (2) | 2.03 (2) | 7.22 (7) | 2.04 (2) | 2.06 (2) | 2.04 (2) | 5.12 (5) | 2.08 (2) | 2.04 (2) |
| Glycine | — | — | 0.99 (1) | — | — | 1.00 (1) | 0.99 (1) | — | — | — | 0.99 (1) | — | — | 1.00 (1) | 0.98 (1) | — |
| Histidine | 0.98 (1) | 0.97 (1) | 0.98 (1) | 0.99 (1) | 0.98 (1) | 0.98 (1) | 0.98 (1) | 0.97 (1) | 0.98 (1) | 0.97 (1) | 0.98 (1) | 0.97 (1) | 0.98 (1) | 0.97 (1) | 0.98 (1) | 0.98 (1) |
| Isoleucine | | | | | | | | | | | | | | | | |
| Leucine | 1.96 (2) | 1.97 (2) | 1.96 (2) | 1.96 (2) | 1.97 (2) | 1.96 (2) | 1.98 (2) | 1.95 (2) | 1.97 (2) | 1.97 (2) | 1.96 (2) | 1.97 (2) | 1.97 (2) | 1.96 (2) | 1.96 (2) | 1.96 (2) |
| Lysine | 3.05 (3) | 1.00 (1) | 1.01 (1) | 1.01 (1) | 2.02 (2) | 2.02 (2) | 1.01 (1) | 2.04 (2) | 3.06 (3) | 1.01 (1) | 1.00 (1) | 1.01 (1) | 2.03 (2) | 2.02 (2) | 1.01 (1) | 2.03 (2) |
| Phenylalanine | 2.03 (2) | 2.04 (2) | 2.03 (2) | 2.03 (2) | 2.02 (2) | 2.02 (2) | 2.04 (2) | 2.03 (2) | 2.03 (2) | 2.04 (2) | 2.05 (2) | 2.03 (2) | 2.02 (2) | 2.04 (2) | 2.03 (2) | 2.03 (2) |
| Proline | 1.02 (1) | 1.03 (1) | 1.02 (1) | 1.02 (1) | 1.03 (1) | 1.02 (1) | 1.03 (1) | 1.02 (1) | 1.01 (1) | 1.02 (1) | 1.02 (1) | 1.02 (1) | 1.02 (1) | 1.03 (1) | 1.02 (1) | 1.03 (1) |
| Serine | 3.91 (4) | 3.92 (4) | 3.94 (4) | 3.93 (4) | 3.95 (4) | 3.92 (4) | 3.93 (4) | 3.94 (4) | 3.95 (4) | 3.92 (4) | 3.93 (4) | 3.95 (4) | 3.96 (4) | 3.91 (4) | 3.92 (4) | 3.92 (4) |
| Threonine | | | | | | | | | | | | | | | | |
| Tyrosine | 1.98 (2) | 1.96 (2) | 1.98 (2) | 1.97 (2) | 1.97 (2) | 1.98 (2) | 1.96 (2) | 1.97 (2) | 1.96 (2) | 1.97 (2) | 1.95 (2) | 1.97 (2) | 1.98 (2) | 1.96 (2) | 1.96 (2) | 1.97 (2) |
| Tryptophan | 1.03 (1) | 1.02 (1) | 1.01 (1) | 1.01 (1) | 1.01 (1) | 1.02 (1) | 1.03 (1) | 1.02 (1) | 1.03 (1) | 1.01 (1) | 1.01 (1) | 1.01 (1) | 1.02 (1) | 1.04 (1) | 1.00 (1) | 1.01 (1) |
| Valine | | 0.97 (1) | | | | | | | | 0.99 (1) | | | | | | |
| H$_2$N—(CH$_2$)$_7$COOH | | | 0.97 (1) | | | | | | | | 0.96 (1) | | | | | |
| H$_2$N—(CH$_2$)$_7$COOH | | | | | | | | | | | | | | | | |

| | 82 | 83 | 84 | 85 | 86 | 87 | 88 | 89 | 90 | 91 | 92 | 93 | 94 | 95 | 96 |
|---|---|---|---|---|---|---|---|---|---|---|---|---|---|---|---|
| | | | | | | | | | Example | | | | | | |
| Molecular weight by FAB method mass spectrum | 3485 (3485.86) | 4074 (4072.27) | 3569 (3567.84) | 3230 (3229.52) | 3471 (3471.80) | 3801 (3801.10) | 4003 (4003.18) | 3544 (3543.90) | 3673 (3672.07) | 4259 (4258.48) | 3755 (3754.05) | 3415 (3415.73) | 3659 (3658.01) | 3988 (3987.31) | 4189 (4189.39) |
| amino acid composition analysis | | | | | | | | | | | | | | | |
| Alanine | 0.97 (1) | 1.01 (1) | 1.00 (1) | 0.99 (1) | 0.98 (1) | 0.99 (1) | 2.96 (3) | 0.97 (1) | 0.99 (1) | 1.00 (1) | 1.00 (1) | 0.99 (1) | 0.98 (1) | 1.01 (1) | 2.97 (3) |
| Arginine | 4.71 (5) | 4.69 (5) | 4.69 (5) | 4.81 (5) | 4.80 (5) | 4.79 (5) | 4.70 (5) | 4.78 (5) | 4.71 (5) | 4.70 (5) | 4.75 (5) | 4.80 (5) | 4.74 (5) | 4.72 (5) | 4.68 (5) |
| Asparagine | 0.91 (1) | 0.92 (1) | 0.93 (1) | 0.90 (1) | 0.91 (1) | 0.92 (1) | 0.93 (1) | 0.91 (1) | 0.89 (1) | 0.90 (1) | 0.91 (1) | 0.92 (1) | 0.93 (1) | 0.90 (1) | 0.89 (1) |
| Aspartic acid | 1.01 (1) | 1.00 (1) | 1.00 (1) | 1.01 (1) | 2.03 (2) | 1.01 (1) | 6.09 (6) | 1.00 (1) | 1.02 (1) | 1.01 (1) | 1.01 (1) | 1.00 (1) | 2.02 (2) | 1.01 (1) | 6.12 (6) |
| Cystine | | | | | | | | | | | | | | | |
| Glutamine | 0.96 (1) | 0.95 (1) | 0.95 (1) | 0.94 (1) | 0.95 (1) | 0.95 (1) | 0.96 (1) | 0.95 (1) | 0.95 (1) | 0.96 (1) | 0.95 (1) | 0.95 (1) | 0.96 (1) | 0.96 (1) | 0.96 (1) |
| Glutamic acid | 2.04 (2) | 7.27 (7) | 2.04 (2) | 2.05 (2) | 2.06 (2) | 5.16 (5) | 2.04 (2) | 2.04 (2) | 2.03 (2) | 7.21 (7) | 2.04 (2) | 2.03 (2) | 2.04 (2) | 5.21 (5) | 2.03 (2) |
| Glycine | — | — | 0.99 (1) | — | — | 0.98 (1) | 1.00 (1) | — | — | — | 1.00 (1) | — | — | 1.00 (1) | 0.99 (1) |
| Histidine | 0.97 (1) | 0.98 (1) | 0.98 (1) | 0.99 (1) | 0.98 (1) | 0.97 (1) | 0.98 (1) | 0.98 (1) | 0.99 (1) | 0.98 (1) | 0.97 (1) | 0.98 (1) | 0.97 (1) | 0.98 (1) | 0.98 (1) |
| Isoleucine | | | | | | | | | | | | | | | |
| Leucine | 1.96 (2) | 1.97 (2) | 1.97 (2) | 1.96 (2) | 1.97 (2) | 1.96 (2) | 1.97 (2) | 1.96 (2) | 1.97 (2) | 1.98 (2) | 1.96 (2) | 1.97 (2) | 1.96 (2) | 1.97 (2) | 1.97 (2) |

TABLE 14-continued

| | | | | | | | | | | | | | | | |
|---|---|---|---|---|---|---|---|---|---|---|---|---|---|---|---|
| Lysine | 3.05 (3) | 1.02 (1) | 1.00 (1) | 1.01 (1) | 2.03 (2) | 2.03 (2) | 1.01 (1) | 2.05 (2) | 3.06 (3) | 1.02 (1) | 1.00 (1) | 1.00 (1) | 2.03 (2) | 2.03 (2) | 1.03 (1) |
| Phenylalanine | 2.04 (2) | 2.02 (2) | 2.03 (2) | 2.03 (2) | 2.04 (2) | 2.01 (2) | 2.04 (2) | 2.02 (2) | 2.04 (2) | 2.04 (2) | 2.03 (2) | 2.02 (2) | 2.03 (2) | 2.02 (2) | 2.02 (2) |
| Proline | 1.02 (1) | 1.02 (1) | 1.02 (1) | 1.03 (1) | 1.03 (1) | 1.03 (1) | 1.02 (1) | 1.02 (1) | 1.02 (1) | 1.03 (1) | 1.02 (1) | 1.01 (1) | 1.02 (1) | 1.03 (1) | 1.03 (1) |
| Serine | 3.94 (4) | 3.95 (4) | 3.92 (4) | 3.91 (4) | 3.93 (4) | 3.93 (4) | 3.94 (4) | 3.91 (4) | 3.94 (4) | 3.93 (4) | 3.92 (4) | 3.90 (4) | 3.89 (4) | 3.91 (4) | 3.92 (4) |
| Threonine | | | | | | | | | | | | | | | |
| Tyrosine | 1.98 (2) | 1.99 (2) | 1.96 (2) | 1.95 (2) | 1.97 (2) | 1.96 (2) | 1.98 (2) | 1.97 (2) | 1.98 (2) | 1.95 (2) | 1.96 (2) | 1.95 (2) | 1.99 (2) | 1.97 (2) | 1.96 (2) |
| Tryptophan | 1.02 (1) | 1.01 (1) | 1.02 (1) | 1.02 (1) | 1.02 (1) | 1.01 (1) | 1.00 (1) | 2.01 (2) | 2.04 (2) | 2.03 (2) | 2.02 (2) | 2.03 (2) | 2.04 (2) | 2.01 (2) | 2.03 (2) |
| Valine | | | | | | | | | | | | | | | |
| $H_2N-(CH_2)_7-COOH$ | — | 0.97 (1) | — | — | — | — | — | — | — | 0.96 (1) | — | — | — | — | — |
| $H_2N-(CH_2)_{11}-COOH$ | — | — | 0.98 (1) | — | — | — | — | — | — | — | 0.99 (1) | — | — | — | — |

Note:
Figures in parenthesis are theoretical value.

EXAMPLE 97

10 g of cellulose particles (sold by Seikagaku Kogyo Co., Ltd., CM-Cellulofine CH) were suspended in 50 ml of anhydrous dioxane (obtained by distilling dioxane commercially available in the presence of metallic sodium) and to the resulting suspension were added 0.5 g of N-hydroxysuccinimide and 1.0 g of dicyclohexyl carbodiimide and then the mixture was shaken at room temperature overnight. The resulting mixture was washed with 0.02 mole/liter of a phosphate buffer solution (pH: 7.4) and filtered with suction. The resulting particles were admixed with 0.02 mole/liter of a phosphate buffer solution (pH: 7.4, 20 ml) containing 20 mg of the peptide obtained in Example 1 and the mixture was stirred at 4° C. overnight. The mixture was filtered with suction. Although the filtrate was subjected to analytical reversed phase high performance liquid chromatography, the remaining unreacted peptide was not observed (immobilization degree of peptide on carrier: about 100%). Like this, about 10 g of the adsorbent wherein 20 mg of the peptide obtained in Example 1 was immobilized on cellulose particles was obtained.

EXAMPLE 98

According to the same manner as that described in Example 97, about 10 g of an adsorbent wherein 18.4 mg of the peptide obtained in Example 9 was immobilized on polyvinyl alcohol particles (immobilization degree of peptide on carrier: about 92%) was obtained except that 10 g of polyvinyl alcohol particles (manufactured by Toso Co., Ltd., Tsk-gel CM-Toyopearl 650C) were used in place of 10 g of cellulose particles and 20 mg of the peptide obtained in Example 9 was used in place of 20 mg of the peptide obtained in Example 1.

EXAMPLE 99

10 g of porous glass particles (manufactured by Electro-nucleonics Corp., U.S.A., CPG-10-1000) were heated under reflux in 100ml of a toluene solution containing 5 ml of γ-aminopropyltriethoxysilane for 24 hours. The resulting mixture was washed with anhydrous dioxane and filtered with suction. The resulting particles were suspended in 100 ml of anhydrous dioxane and to the suspension was added 3 g of succinic anhydride. Then the mixture was stirred at room temperature overnight. The resulting mixture was washed with anhydrous dioxane and filtered with suction. The resulting particles were suspended in 50 ml of anhydrous dioxane and to the suspension was added 0.5 g of N-hydroxysuccinimide and 1.0 g of dicyclohexylcarbodiimide. The mixture was stirred at room temperature overnight. The resulting mixture was washed with 0.02 mole/liter of a phosphate buffer solution (pH: 7.4) and filtered with suction. The resulting particles were admixed with 0.02 mole/liter of a phosphate buffer solution containing 20 mg of the peptide obtained in Example 17 (pH: 7.4, 20 ml) and this mixture was stirred at 4° C overnight. The mixture was filtered with suction to obtain about 10 g of an absorbent wherein 20 mg of the peptide obtained in Example 17 was immobilized on the porous glass particle (immobilization degree of peptide on carrier: about 100%).

EXAMPLES 100 TO 192

According to any one of manners as those described in Examples 97 to 99, adsorbents wherein peptides were immobilized on the granular carriers were obtained except that 20 mg of the peptides shown in Table 10 were used. The granular carriers used and immobilization degrees of peptide on carriers are shown in Table 15, respectively.

TABLE 15

| Example | Peptide | Granular carrier | Immobilization degree (%) |
|---|---|---|---|
| 100 | obtained in Example 2 | cellulose particles | about 98 |
| 101 | obtained in Example 3 | " | about 90 |
| 102 | obtained in Example 4 | " | about 85 |
| 103 | obtained in Example 5 | " | about 75 |
| 104 | obtained in Example 6 | " | about 92 |
| 105 | obtained in Example 7 | polyvinyl alcohol particles | about 95 |
| 106 | obtained in Example 8 | cellulose particles | about 95 |
| 107 | obtained in Example 10 | polyvinyl alcohol particles | about 100 |
| 108 | obtained in Example 11 | " | about 98 |
| 109 | obtained in Example 12 | cellulose particles | about 92 |
| 110 | obtained in Example 13 | " | about 80 |
| 111 | obtained in Example 14 | " | about 88 |
| 112 | obtained in Example 15 | " | about 90 |
| 113 | obtained in Example 16 | " | about 92 |
| 114 | obtained in Example 18 | " | about 100 |
| 115 | obtained in Example 19 | " | about 95 |
| 116 | obtained in Example 20 | " | about 93 |
| 117 | obtained in Example 21 | porous glass particles | about 85 |
| 118 | obtained in Example 22 | " | about 100 |
| 119 | obtained in Example 23 | " | about 100 |
| 120 | obtained in Example 24 | cellulose particles | about 94 |
| 121 | obtained in Example 25 | porous glass particles | about 98 |
| 122 | obtained in Example 26 | cellulose particles | about 100 |
| 123 | obtained in Example 27 | " | about 96 |
| 124 | obtained in Example 28 | " | about 96 |
| 125 | obtained in Example 29 | " | about 92 |
| 126 | obtained in Example 30 | " | about 96 |
| 127 | obtained in Example 31 | " | about 99 |
| 128 | obtained in Example 32 | " | about 93 |
| 129 | obtained in Example 33 | " | about 100 |
| 130 | obtained in Example 34 | " | about 98 |
| 131 | obtained in Example 35 | " | about 90 |
| 132 | obtained in Example 36 | " | about 85 |
| 133 | obtained in Example 37 | " | about 75 |

TABLE 15-continued

| Example | Peptide | Granular carrier | Immobilization degree (%) |
|---|---|---|---|
| 134 | obtained in Example 38 | " | about 92 |
| 135 | obtained in Example 39 | polyvinyl alcohol particles | about 95 |
| 136 | obtained in Example 40 | cellulose particles | about 95 |
| 137 | obtained in Example 41 | polyvinyl alcohol particles | about 92 |
| 138 | obtained in Example 42 | " | about 100 |
| 139 | obtained in Example 43 | " | about 98 |
| 140 | obtained in Example 44 | cellulose particles | about 92 |
| 141 | obtained in Example 45 | " | about 80 |
| 142 | obtained in Example 46 | " | about 88 |
| 143 | obtained in Example 47 | " | about 90 |
| 144 | obtained in Example 48 | " | about 92 |
| 145 | obtained in Example 49 | " | about 100 |
| 146 | obtained in Example 50 | " | about 100 |
| 147 | obtained in Example 51 | " | about 95 |
| 148 | obtained in Example 52 | " | about 93 |
| 149 | obtained in Example 53 | porous glass particles | about 85 |
| 150 | obtained in Example 54 | " | about 100 |
| 151 | obtained in Example 55 | " | about 100 |
| 152 | obtained in Example 56 | cellulose particles | about 94 |
| 153 | obtained in Example 57 | " | about 100 |
| 154 | obtained in Example 58 | " | about 92 |
| 155 | obtained in Example 59 | " | about 92 |
| 156 | obtained in Example 60 | " | about 90 |
| 157 | obtained in Example 61 | " | about 90 |
| 158 | obtained in Example 62 | " | about 95 |
| 159 | obtained in Example 63 | polyvinyl alcohol particles | about 96 |
| 160 | obtained in Example 64 | " | about 89 |
| 161 | obtained in Example 65 | porous glass particles | about 98 |
| 162 | obtained in Example 66 | " | about 100 |
| 163 | obtained in Example 67 | polyvinyl alcohol particles | about 90 |
| 164 | obtained in Example 68 | " | about 88 |
| 165 | obtained in Example 69 | " | about 93 |
| 166 | obtained in Example 70 | cellulose particles | about 95 |
| 167 | obtained in Example 71 | " | about 94 |
| 168 | obtained in Example 72 | " | about 88 |
| 169 | obtained in Example 73 | " | about 99 |
| 170 | obtained in Example 74 | " | about 100 |
| 171 | obtained in Example 75 | porous glass particles | about 98 |
| 172 | obtained in Example 76 | polyvinyl alcohol particles | about 91 |
| 173 | obtained in Example 77 | " | about 85 |
| 174 | obtained in Example 78 | cellulose particle | about 93 |
| 175 | obtained in Example 79 | " | about 96 |
| 176 | obtained in Example 80 | " | about 85 |
| 177 | obtained in Example 81 | " | about 98 |
| 178 | obtained in Example 82 | " | about 100 |
| 179 | obtained in Example 83 | polyvinyl alcohol particles | about 88 |
| 180 | obtained in Example 84 | " | about 85 |
| 181 | obtained in Example 85 | " | about 82 |
| 182 | obtained in Example 86 | cellulose particles | about 99 |
| 183 | obtained in Example 87 | " | about 95 |
| 184 | obtained in Example 88 | " | about 90 |
| 185 | obtained in Example 89 | porous glass particles | about 98 |
| 186 | obtained in Example 90 | polyvinyl alcohol particles | about 100 |
| 187 | obtained in Example 91 | " | about 90 |
| 188 | obtained in Example 92 | cellulose particles | about 88 |
| 189 | obtained in Example 93 | " | about 89 |
| 190 | obtained in Example 94 | " | about 94 |
| 191 | obtained in Example 95 | " | about 98 |
| 192 | obtained in Example 96 | " | about 89 |

EXPERIMENT 1

Obtaining IL-6 receptor expression cells

A human lymphocyte fraction was obtained from human peripheral blood with Ficoll-Paque (manufactured by Pharmacia-LKB). The fraction was reacted with a cultured supernatant of Epstein-Barr Virus producing cell strain B958 to transform the human lymphocytes to obtain IL-6 receptor expression cells.

Preparation of FITC labeled anti-IL-6 antibody 1 mg of anti-human IL-6 antibody [Rabbit Anti-human Interleukin-6, manufactured by Genzyme Corp.] was dissolved in a 0.05M carbonate buffer solution (pH: 9.5) and to the resulting solution was added 10 μg of FITC [Fluorescein isothiocyanate, manufactured by Sigma Corp.]. The mixture was stirred at 4° C. overnight. The resulting solution was passed through PD-10 column (manufactured by Pharmacia-LKB) to obtain FITC labeled anti-IL-6 antibody as a firstly eluted fraction.

Activity for inhibition of binding of IL-6 to receptor by peptide $10^5$ IL-6 receptor expression cells were suspended in 0.5 % BSA (bovine serum albumin, manufactured by Sigma Corp.)-PBS (a phosphate buffer solution containing 0.15 M sodium chloride, pH 7.4) and to the resulting suspension were added 50 ng of IL-6 (Human recombinant interleukin-6, manufactured by Genzyme Corp.)

and 5 μg of the peptide obtained in any one of Examples 1 to 96. The suspension was allowed to stand at 4° C for one hour. Then, after washing the cells centrifugally with 0.5% BSA-PBS three times (1200 rpm, 5 min.), 1 μg of FITC labeled anti-IL-6 antibody was added and the mixture was allowed to stand at 4° C. for 30 minutes. After washing with 0.5% BSA-PBS three times, the intensity of fluorescence of the cells was determined. The binding inhibition activity of the peptide of each Example was evaluated, by taking the value obtained without addition of the peptide as a control and taking the value obtained without addition of IL-6 as a blank, according to the following formula:

$$\text{Binding inhibition activity (\%)} = \left( \frac{\text{Intensity of fluorescence of control} - \text{Intensity of fluorescence when peptide being added}}{\text{Intensity of fluorescence of control} - \text{Intensity of fluorescence of blank}} \right) \times 100$$

The results obtained for the peptides of Examples 1 to 96 are shown in Table 16.

TABLE 16

| Peptide | Binding inhibition activity (%) |
|---|---|
| peptide obtained in Example 1 | 38 |
| peptide obtained in Example 2 | 35 |
| peptide obtained in Example 3 | 40 |
| peptide obtained in Example 4 | 42 |
| peptide obtained in Example 5 | 28 |
| peptide obtained in Example 6 | 36 |
| peptide obtained in Example 7 | 38 |
| peptide obtained in Example 8 | 37 |
| peptide obtained in Example 9 | 30 |
| peptide obtained in Example 10 | 28 |
| peptide obtained in Example 11 | 34 |
| peptide obtained in Example 12 | 35 |
| peptide obtained in Example 13 | 25 |
| peptide obtained in Example 14 | 32 |
| peptide obtained in Example 15 | 30 |
| peptide obtained in Example 16 | 31 |
| peptide obtained in Example 17 | 60 |
| peptide obtained in Example 18 | 55 |
| peptide obtained in Example 19 | 62 |
| peptide obtained in Example 20 | 65 |
| peptide obtained in Example 21 | 52 |
| peptide obtained in Example 22 | 58 |
| peptide obtained in Example 23 | 58 |
| peptide obtained in Example 24 | 55 |
| peptide obtained in Example 25 | 45 |
| peptide obtained in Example 26 | 42 |
| peptide obtained in Example 27 | 48 |
| peptide obtained in Example 28 | 47 |
| peptide obtained in Example 29 | 41 |
| peptide obtained in Example 30 | 46 |
| peptide obtained in Example 31 | 48 |
| peptide obtained in Example 32 | 44 |
| peptide obtained in Example 33 | 58 |
| peptide obtained in Example 34 | 55 |
| peptide obtained in Example 35 | 60 |
| peptide obtained in Example 36 | 62 |
| peptide obtained in Example 37 | 48 |
| peptide obtained in Example 38 | 56 |
| peptide obtained in Example 39 | 58 |
| peptide obtained in Example 40 | 37 |
| peptide obtained in Example 41 | 30 |
| peptide obtained in Example 42 | 28 |
| peptide obtained in Example 43 | 34 |
| peptide obtained in Example 44 | 35 |
| peptide obtained in Example 45 | 25 |
| peptide obtained in Example 46 | 32 |
| peptide obtained in Example 47 | 30 |
| peptide obtained in Example 48 | 31 |
| peptide obtained in Example 49 | 30 |
| peptide obtained in Example 50 | 25 |
| peptide obtained in Example 51 | 32 |
| peptide obtained in Example 52 | 35 |
| peptide obtained in Example 53 | 22 |
| peptide obtained in Example 54 | 28 |
| peptide obtained in Example 55 | 28 |
| peptide obtained in Example 56 | 25 |
| peptide obtained in Example 57 | 63 |
| peptide obtained in Example 58 | 60 |
| peptide obtained in Example 59 | 60 |
| peptide obtained in Example 60 | 58 |
| peptide obtained in Example 61 | 45 |
| peptide obtained in Example 62 | 50 |
| peptide obtained in Example 63 | 51 |
| peptide obtained in Example 64 | 55 |
| peptide obtained in Example 65 | 68 |
| peptide obtained in Example 66 | 65 |
| peptide obtained in Example 67 | 51 |
| peptide obtained in Example 68 | 55 |
| peptide obtained in Example 69 | 54 |
| peptide obtained in Example 70 | 59 |
| peptide obtained in Example 71 | 60 |
| peptide obtained in Example 72 | 57 |
| peptide obtained in Example 73 | 71 |
| peptide obtained in Example 74 | 70 |
| peptide obtained in Example 75 | 63 |
| peptide obtained in Example 76 | 58 |
| peptide obtained in Example 77 | 58 |
| peptide obtained in Example 78 | 60 |
| peptide obtained in Example 79 | 62 |
| peptide obtained in Example 80 | 59 |
| peptide obtained in Example 81 | 76 |
| peptide obtained in Example 82 | 70 |
| peptide obtained in Example 83 | 63 |
| peptide obtained in Example 84 | 65 |
| peptide obtained in Example 85 | 60 |
| peptide obtained in Example 86 | 58 |
| peptide obtained in Example 87 | 72 |
| peptide obtained in Example 88 | 66 |
| peptide obtained in Example 89 | 68 |
| peptide obtained in Example 90 | 71 |
| peptide obtained in Example 91 | 60 |
| peptide obtained in Example 92 | 62 |
| peptide obtained in Example 93 | 59 |
| peptide obtained in Example 94 | 63 |
| peptide obtained in Example 95 | 65 |
| peptide obtained in Example 96 | 52 |

EXPERIMENT 2

Preparation of biotin labeled anti-IL-6 antibody

200 μg of the same anti-IL-6 antibody as that used in Experiment 1 was dissolved in 0.2 ml of a 0.1M NaHCO$_3$ aqueous solution. To the resulting solution was added 20 μg of a solution of NHS-LS-biotin [manufactured by Pierce Corp.] in DMF (1 mg/ml) and the mixture was allowed to react at room temperature for 4 hours. The reaction mixture was dialyzed to PBS at 4° C. to obtain a biotin labeled anti-IL-6 antibody.

Adsorption of IL-6 in serum 50 mg of the adsorbent obtained in any one of Examples 97 to 192 was shaken with 500 μl of serum from a patient with rheumatism containing IL-6 at 37° C. for 3 hours and the supernatant was used as a test solution.

Measurement of IL-6 concentration in test solution and evaluation of adsorbability of adsorbent The same anti-IL-6-antibody as that used in Experiment 1 was immobilized in each well of a flat bottom 96 well-plate [Falcon Rigid-Assay Plate, manufactured by Becton Dickinson Corp.] in an amount of 2.5 μg/well. After blocking each well with 1% BSA-PBS, 50 μl portions of the test solution were distributed into wells.

After standing at 4° C. overnight, each well was washed and 0.5 μl portions of biotin labeled anti-IL-6 antibody were distributed into wells. The plate was further allowed to stand at 37° C. for one hour. After washing each well, HRP labeled streptoavidin [1500-fold dilution, manufactured by Kirkegaard & Perry Lab. Inc.] was distributed into each well and the plate was further allowed to stand at 37° C. for 30 minutes. After washing each well, ABTS was added in the presence of $H_2O_2$ to develop color and difference between absorbances at 409 nm and 501 nm of each well was measured. A calibration curve was prepared from the absorbances of wells wherein solutions containing a known concentration of human IL-6 were added in place of the test solution and IL-6 concentration in each test solution was determined by using the calibration curve. An adsorption removal rate of IL-6 was calculated by using the IL-6 concentration obtained by using an adsorbent, wherein glycine was immobilized on cellulose particles in place of peptide as a control value, according to the following formula:

$$\text{Adsorption removal rate (\%)} = \left( \frac{\text{Control value} - \text{Concentration in test solution}}{\text{Control value}} \right) \times 100$$

The results are shown in Table 17.

TABLE 17

| Absorbent | Adsorption removal rate (%) |
| --- | --- |
| obtained in Example 97 | 60 |
| obtained in Example 98 | 52 |
| obtained in Example 99 | 85 |
| obtained in Example 100 | 58 |
| obtained in Example 101 | 55 |
| obtained in Example 102 | 57 |
| obtained in Example 103 | 50 |
| obtained in Example 104 | 53 |
| obtained in Example 105 | 59 |
| obtained in Example 106 | 50 |
| obtained in Example 107 | 55 |
| obtained in Example 108 | 53 |
| obtained in Example 109 | 45 |
| obtained in Example 110 | 54 |
| obtained in Example 111 | 54 |
| obtained in Example 112 | 49 |
| obtained in Example 113 | 82 |
| obtained in Example 114 | 80 |
| obtained in Example 115 | 83 |
| obtained in Example 116 | 82 |
| obtained in Example 117 | 72 |
| obtained in Example 118 | 84 |
| obtained in Example 119 | 81 |
| obtained in Example 120 | 79 |
| obtained in Example 121 | 65 |
| obtained in Example 122 | 63 |
| obtained in Example 123 | 68 |
| obtained in Example 124 | 70 |
| obtained in Example 125 | 58 |
| obtained in Example 126 | 62 |
| obtained in Example 127 | 65 |
| obtained in Example 128 | 63 |
| obtained in Example 129 | 60 |
| obtained in Example 130 | 58 |
| obtained in Example 131 | 55 |
| obtained in Example 132 | 57 |
| obtained in Example 133 | 50 |
| obtained in Example 134 | 53 |
| obtained in Example 135 | 39 |
| obtained in Example 136 | 30 |
| obtained in Example 137 | 52 |
| obtained in Example 138 | 35 |
| obtained in Example 139 | 33 |
| obtained in Example 140 | 25 |
| obtained in Example 141 | 34 |
| obtained in Example 142 | 24 |
| obtained in Example 143 | 29 |
| obtained in Example 144 | 32 |
| obtained in Example 145 | 85 |
| obtained in Example 146 | 30 |
| obtained in Example 147 | 33 |
| obtained in Example 148 | 32 |
| obtained in Example 149 | 22 |
| obtained in Example 150 | 34 |
| obtained in Example 151 | 31 |
| obtained in Example 152 | 29 |
| obtained in Example 153 | 81 |
| obtained in Example 154 | 79 |
| obtained in Example 155 | 75 |
| obtained in Example 156 | 79 |
| obtained in Example 157 | 66 |
| obtained in Example 158 | 71 |
| obtained in Example 159 | 68 |
| obtained in Example 160 | 75 |
| obtained in Example 161 | 86 |
| obtained in Example 162 | 85 |
| obtained in Example 163 | 70 |
| obtained in Example 164 | 78 |
| obtained in Example 165 | 72 |
| obtained in Example 166 | 80 |
| obtained in Example 167 | 79 |
| obtained in Example 168 | 77 |
| obtained in Example 169 | 90 |
| obtained in Example 170 | 88 |
| obtained in Example 171 | 81 |
| obtained in Example 172 | 79 |
| obtained in Example 173 | 77 |
| obtained in Example 174 | 78 |
| obtained in Example 175 | 81 |
| obtained in Example 176 | 77 |
| obtained in Example 177 | 93 |
| obtained in Example 178 | 89 |
| obtained in Example 179 | 81 |
| obtained in Example 180 | 83 |
| obtained in Example 181 | 77 |
| obtained in Example 182 | 77 |
| obtained in Example 183 | 72 |
| obtained in Example 184 | 66 |
| obtained in Example 185 | 88 |
| obtained in Example 186 | 90 |
| obtained in Example 187 | 78 |
| obtained in Example 188 | 81 |
| obtained in Example 189 | 79 |
| obtained in Example 190 | 82 |
| obtained in Example 191 | 86 |
| obtained in Example 192 | 75 |

INDUSTRIAL APPLICABILITY

According to the present invention, there is provided a peptide of the general formula (I) useful in the treatment of autoimmune disease. Since the peptide of the general formula (I) inhibits binding of IL-6 to its receptor, administration of the peptide to a patient with an autoimmune disease is effective for inhibiting the production of autoimmune antibody caused by binding of IL-6 to its receptor.

Further, according to the present invention, there is provided an adsorbent wherein the peptide of the general formula (I) is immobilized on an insoluble carrier. The absorbent can be used for removing IL-6 from a patient with an autoimmune disease by extracorporeal blood circulation system using the absorbent.

What is claimed is:

1. A peptide being capable of binding to interleukin 6 represented by the general formula:

H-X-A-Y-Z wherein A is a peptide segment selected from the group consisting of a peptide segment of the formula: -Gly-Thr-Val-His-Leu-Leu-Val-Asp-Val-Pro-Pro-Glu-Glu-Pro-Gln-Leu-Ser-Cys-Phe-Arg-Lys-, a peptide segment of the formula: -Arg-Lys-Phe-Gln-Asn-Ser-Pro-Ala-Glu-Asp-Phe-Gln-Glu-Pro-Cys-Gln-Tyr-Ser-Gln-Glu-Ser-, a peptide segment of the formula: -Thr-Ser-Leu-Pro-Gly-Asp-Ser-Val-Thr-Leu-Thr-Cys-Pro-Gly-Val-Glu-Pro-Glu-Asp-, a peptide segment of the formula: -Gln-Ala-Leu-Thr-Thr-Asn-Lys-Asp-Asp-Asp-Asn-Ile-Leu-Phe-Arg-Asp-Ser-Ala-, a peptide segment of the formula: -Trp-Asn-Ser-Ser-Phe-Tyr-Arg-Leu-Arg-Phe-Glu-Leu-Arg-Tyr-Arg-Ala-Glu-Arg-Ser-Lys, a peptide segment of the formula: -Ser-Thr-Pro-Ser-Leu-Thr-Thr-Lys-Ala-Val-Leu-Leu-Val-Arg-Lys-Phe-Gln-Asn-Ser-Pro-Ala-Glu-Asp-, a peptide segment of the formula: -Asn-Pro-Arg-Trp-Leu-Ser-Val-Thr-Trp-Gln-Asp-Pro-His-Ser-, a peptide segment of the formula: -His-Ser-Trp-Asn-Ser-Ser-Phe-Tyr-Arg-Leu-Arg-Phe-Glu-Leu-Arg-Tyr-Arg-Ala-Glu-Arg-Ser-Lys, a peptide segment of the formula: -Pro-His-Ser-Trp-Asn-Ser-Ser-Phe-Tyr-Arg-Leu-Arg-Phe-Glu-Leu-Arg-Tyr-Arg-Ala-Glu-Arg-Ser-Lys-, a peptide segment of the formula: -Asp-Pro-His-Ser-Trp-Asn-Ser-Ser-Phe-Tyr-Arg-Leu-Arg-Phe-Glu-Leu-Arg-Tyr-Arg-Ala-Glu-Arg-Ser-Lys-, a peptide segment of the formula: -Gln-Asp-Pro-His-Ser-Trp-Asn-Ser-Ser-Phe-Tyr-Arg-Leu-Arg-Phe-Glu-Leu-Arg-Tyr-Arg-Ala-Glu-Arg-Ser-Lys-, and a peptide segment of the formula: -Trp-Gln-Asp-Pro-His-Ser-Trp-Asn-Ser-Ser-Phe-Tyr-Arg-Leu-Arg-Phe-Glu-Leu-Arg-Tyr-Arg-Ala-Glu-Arg-Ser-Lys-;

each of X and Y is a single bond or an amino acid residue selected from the group consisting of Asp, Glu, Lys, Ala and a divalent group of the formula: -NH(CH$_2$)$_n$-CO- (wherein n is an integer of 1 to 17), or a peptide segment composed of 2 to 10 amino acid residues selected from the above group bound to each other through a peptide bond; and Z is a hydroxyl group or an amino group.

2. A peptide according to claim 1, wherein A is a peptide segment of the formula: -Gly-Thr-Val-His-Leu-Leu-Val-Asp-Val-Pro-Pro-Glu-Glu-Pro-Gln-Leu-Ser-Cys-Phe-Arg-Lys-.

3. A peptide according to claim 1, wherein A is a peptide segment of the formula: -Arg-Lys-Phe-Gln-Asn-Ser-Pro-Ala-Glu-Asp-Phe-Gln-Glu-Pro-Cys-Gln-Tyr-Ser-Gln-Glu-Ser-.

4. A peptide according to claim 1, wherein A is a peptide segment of the formula: -Thr-Ser-Leu-Pro-Gly-Asp-Ser-Val-Thr-Leu-Thr-Cys-Pro-Gly-Val-Glu-Pro-Glu-Asp-.

5. A peptide according to claim 1, wherein A is a peptide segment of the formula: -Gln-Ala-Leu-Thr-Thr-Asn-Lys-Asp-Asp-Asp-Asn-Ile-Leu-Phe-Arg-Asp-Ser-Ala-.

6. A peptide according to claim 1, wherein A is a peptide segment of the formula: -Trp-Asn-Ser-Ser-Phe-Tyr-Arg-Leu-Arg-Phe-Glu-Leu-Arg-Tyr-Arg-Ala-Glu-Arg-Ser-Lys.

7. A peptide according to claim 1, wherein A is a peptide segment of the formula: -Ser-Thr-Pro-Ser-Leu-Thr-Thr-Lys-Ala-Val-Leu-Leu-Val-Arg-Lys-Phe-Gln-Asn-Ser-Pro-Ala-Glu-Asp-.

8. A peptide according to claim 1, wherein A is a peptide segment of the formula: -Asn-Pro-Arg-Trp-Leu-Ser-Val-Thr-Trp-Gln-Asp-Pro-His-Ser-.

9. A peptide according to claim 1, wherein A is a peptide segment of the formula: -His-Ser-Trp-Asn-Ser-Ser-Phe-Tyr-Arg-Leu-Arg-Phe-Glu-Leu-Arg-Tyr-Arg-Ala-Glu-Arg-Ser-Lys.

10. A peptide according to claim 1, wherein A is a peptide segment of the formula: -Pro-His-Ser-Trp-Asn-Ser-Ser-Phe-Tyr-Arg-Leu-Arg-Phe-Glu-Leu-Arg-Tyr-Arg-Ala-Glu-Arg-Ser-Lys-.

11. A peptide according to claim 1, wherein A is a peptide segment of the formula: -Asp-Pro-His-Ser-Trp-Asn-Ser-Ser-Phe-Tyr-Arg-Leu-Arg-Phe-Glu-Leu-Arg-Tyr-Arg-Ala-Glu-Arg-Ser-Lys-.

12. A peptide according to claim 1, wherein A is a peptide segment of the formula: -Gln-Asp-Pro-His-Ser-Trp-Asn-Ser-Ser-Phe-Tyr-Arg-Leu-Arg-Phe-Glu-Leu-Arg-Tyr-Arg-Ala-Glu-Arg-Ser-Lys-.

13. A peptide according to claim 1, wherein A is a peptide segment of the formula: -Trp-Gln-Asp-Pro-His-Ser-Trp-Asn-Ser-Ser-Phe-Tyr-Arg-Leu-Arg-Phe-Glu-Leu-Arg-Tyr-Arg-Ala-Glu-Arg-Ser-Lys-.

14. An adsorbent comprising the peptide according to claim 1 immobilized on a carrier.

15. An adsorbent comprising the peptide according to claim 2 immobilized on a carrier.

16. An adsorbent comprising the peptide according to claim 3 immobilized on a carrier.

17. An adsorbent comprising the peptide according to claim 4 immobilized on a carrier.

18. An adsorbent comprising the peptide according to claim 5 immobilized on a carrier.

19. An adsorbent comprising the peptide according to claim 6 immobilized on a carrier.

20. An adsorbent comprising the peptide according to claim 7 immobilized on a carrier.

21. An adsorbent comprising the peptide according to claim 8 immobilized on a carrier.

22. An adsorbent comprising the peptide according to claim 9 immobilized on a carrier.

23. An adsorbent comprising the peptide according to claim 10 immobilized on a carrier.

24. An adsorbent comprising the peptide according to claim 11 immobilized on a carrier.

25. An adsorbent comprising the peptide according to claim 12 immobilized on a carrier.

26. An adsorbent comprising the peptide according to claim 13 immobilized on a carrier.

* * * * *